United States Patent
Hossain et al.

(10) Patent No.: US 9,878,305 B2
(45) Date of Patent: Jan. 30, 2018

(54) FLUIDIZABLE VANADIUM CATALYST FOR OXIDATIVE DEHYDROGENATION OF ALKANES TO OLEFINS IN A GAS PHASE OXYGEN FREE ENVIRONMENT

(71) Applicant: KING FAHD UNIVERSITY OF PETROLEUM AND MINERALS, Dhahran (SA)

(72) Inventors: Mohammad M. Hossain, Dhahran (SA); Afees A. Ayandiran, Dhahran (SA); Shaikh A. Razzak, Dhahran (SA); Housam Binous, Dhahran (SA)

(73) Assignee: King Fahd University of Petroleum and Minerals, Dhahran (SA)

( * ) Notice: Subject to any disclaimer, the term of this patent is extended or adjusted under 35 U.S.C. 154(b) by 0 days.

(21) Appl. No.: 15/182,248

(22) Filed: Jun. 14, 2016

(65) Prior Publication Data
US 2017/0354955 A1    Dec. 14, 2017

(51) Int. Cl.
*B01J 21/04*    (2006.01)
*B01J 23/22*    (2006.01)
(Continued)

(52) U.S. Cl.
CPC ............ *B01J 23/22* (2013.01); *B01J 23/02* (2013.01); *B01J 35/0006* (2013.01);
(Continued)

(58) Field of Classification Search
CPC ... B01J 21/04; B01J 23/02; B01J 23/22; B01J 35/0006; B01J 35/023; B01J 35/026;
(Continued)

(56) References Cited

U.S. PATENT DOCUMENTS 2,422,172 A * 6/1947 Beeck ...................... B01J 21/16
                                                      208/135
3,207,808 A * 9/1965 Bajars ........................ C07C 5/56
                                                      502/224
(Continued)

FOREIGN PATENT DOCUMENTS

CA    2733278 A1 *    2/2010    .............. B01J 23/14
EP    1916230 B1    12/2009

OTHER PUBLICATIONS

Putra, M.D., et al., "Oxidative Dehydrogenation of Propane to Propylene over Al2O3-Supported Sr—V—Mo Catalysts", Catalysis Communications, vol. 14, pp. 107-110, (Aug. 6, 2011).
De, M., et al., "Effect of Calcium and Potassium on V2O5/ZrO2 Catalyst for Oxidative Dehydrogenation of Propane: A Comparative Study", Catalysis Letters, vol. 102, Nos. 3-4, pp. 237-246, (2005).
Murgia, V., et al., Oxidative Dehydrogenation of Propane and N-Butane over Aluminia Supported Vanadium Catalysts, URL: http://www.scielo.org.ar/scielo.php?script=sci_arttext&pid=S0327-07932004000200002, Latin American Applied Research, vol. 34, No. 2, 8 Pages total, (Jun. 2004).
(Continued)

*Primary Examiner* — Patricia L. Hailey
(74) *Attorney, Agent, or Firm* — Oblon, McClelland, Maier & Neustadt, L.L.P.

(57) ABSTRACT

Fluidizable catalysts for the gas phase oxygen-free oxidative dehydrogenation of alkanes, such as propane, to corresponding olefins, such as propylene. The catalysts comprise 5-20% by weight per total catalyst weight of one or more vanadium oxides ($VO_x$), such as $V_2O_5$. The dehydrogenation catalysts are disposed on an alumina support that is modified with calcium oxide to influence characteristics of lattice oxygen at the catalyst surface. Various methods of preparing and characterizing the catalyst as well as methods for the gas phase oxygen free oxidative dehydrogenation of alkanes, such as propane, to corresponding olefins, such as propylene, with improved alkane conversion and olefin product selectivity are also disclosed.

19 Claims, 19 Drawing Sheets

(51) Int. Cl.
  *B01J 23/02* (2006.01)
  *B01J 35/00* (2006.01)
  *B01J 35/02* (2006.01)
  *B01J 35/10* (2006.01)
  *B01J 37/04* (2006.01)
  *B01J 37/18* (2006.01)
  *B01J 37/14* (2006.01)
  *C07C 5/48* (2006.01)

(52) U.S. Cl.
  CPC ......... *B01J 35/0026* (2013.01); *B01J 35/026* (2013.01); *B01J 35/1009* (2013.01); *B01J 35/1014* (2013.01); *B01J 37/04* (2013.01); *B01J 37/14* (2013.01); *B01J 37/18* (2013.01); *C07C 5/48* (2013.01); *C07C 2521/04* (2013.01); *C07C 2523/02* (2013.01); *C07C 2523/22* (2013.01)

(58) Field of Classification Search
  CPC ..... B01J 35/1009; B01J 35/1014; C07C 5/48; C07C 2521/04; C07C 2523/02; C07C 2523/22
  USPC .......................... 502/353, 354; 585/664, 661
  See application file for complete search history.

(56) References Cited

U.S. PATENT DOCUMENTS

| | | | |
|---|---|---|---|
| 2003/0166984 A1* | 9/2003 | Park | C07C 5/3332 585/444 |
| 2007/0225532 A1* | 9/2007 | Tonkovich | C07C 5/3332 585/444 |
| 2013/0072737 A1 | 3/2013 | Kustov et al. | |
| 2013/0165702 A1* | 6/2013 | Weiner | C07C 29/149 568/885 |
| 2013/0165703 A1* | 6/2013 | Weiner | C07C 29/149 568/885 |
| 2015/0224482 A1 | 8/2015 | Cizeron et al. | |

OTHER PUBLICATIONS

Al-Ghamdi, S.A., et al., "Propylene Production via Propane Oxidative Dehydrogenation over VOx/c-Al2O3 Catalyst", Fuel, vol. 128, pp. 120-140, (2014).

Ayandiran, A.A., et al., "Oxidative Dehydrogenation of Propane to Propylene over VOx/CaO-γAl2O3 using Lattice Oxygen", Catalysis Science & Technology, 14 Pages total, (Mar. 7, 2016).

* cited by examiner

FLUIDIZABLE VANADIUM CATALYST FOR OXIDATIVE DEHYDROGENATION OF ALKANES TO OLEFINS IN A GAS PHASE OXYGEN FREE ENVIRONMENT

BACKGROUND OF THE INVENTION

Technical Field

The present disclosure relates to fluidizable vanadium based $VO_x/CaO$-γ-$Al_2O_3$ catalysts and dehydrogenation processes using the catalysts for the oxidative dehydrogenation of alkanes, such as propane to propylene, in the absence of gas phase oxygen.

Description of the Related Art

The "background" description provided herein is for the purpose of generally presenting the context of the disclosure. Work of the presently named inventors, to the extent it is described in this background section, as well as aspects of the description which may not otherwise qualify as prior art at the time of filing, are neither expressly or impliedly admitted as prior art against the present invention.

Propylene is an important precursor and feedstock in the chemical industry used to produce many different valuable products. Approximately two thirds of the propylene produced worldwide is consumed in the production of thermoplastic polypropylene which is commonly used in the fabrication of household appliances, plastic films and many other applications. With the increasing world population and the improving quality of human life, worldwide propylene demand/sales has reached over ninety billion dollars ["Market Study: Propylene, Ceresana Research, February 2011." ceresana.com. Retrieved 2011-02-13]. Conventionally, propylene has been produced from petroleum refining and olefin cracking processes. In order to meet the ever increasing demands for petroleum fuel and olefins (propylene, ethylene, etc.) there is a growing need to develop alternative propylene production technology. In this regard, propylene from propane, available both in natural gas and refinery off gases, is considered an attractive technology. The abundant availability of propane in different parts of the world including the United States and the Middle Eastern Region can make these intentional propylene productions largely sustainable as compared to refinery and olefin cracker processes [Ashford's Dictionary of Industrial Chemicals, Third Edition, 2011, ISBN 978-0-9522674-3-0, pages 7766-9].

At present, there are three major commercial processes available in the production of propylene, including steam cracking, fluid catalytic cracking (FCC) and catalytic dehydrogenation. Steam cracking processes consume a large amount of heat energy, which accounts for 70% of the overall production cost. Coke formation during the cracking of heavy hydrocarbon molecules is an additional drawback of the steam cracking process. This coke formation causes severe operational constraints on the process, especially fouling, which requires frequent plant shut downs for cleaning. In contrast, in the catalytic cracking (FCC) process the coke generation is deliberate. The formed coke is combusted in the catalyst regenerator producing heat energy that is supplied back to the catalytic cracking unit using the catalyst as an energy carrier. This energy is essential for the FCC reactor to carry out the endothermic cracking reactions. In the FCC process the propylene is obtained as a byproduct, in addition to the lighter gasoline and other fuels. The yield of propylene can be increased by manipulating the FCC operating conditions and using catalysts as additives. Recent research shows that the FCC catalysts can improve the propylene yield by about 4.5% to 10%. However, the propylene production cost in the FCC process is still high due to the energy required by the endothermic cracking reactions. This high energy demand and the continuous catalyst regeneration, make the FCC process a capital intensive one. Consequently, the building of a FCC system for the sole aim of producing propylene is not economically viable. The third available technology, catalytic dehydrogenation, also suffers from the problems of coke formation and high energy requirements as a result of the endothermic nature of the reaction [S. A. Al-Ghamdi (2013) oxygen-free propane oxidative dehydrogenation over vanadium oxide catalysts: reactivity and kinetic modeling. Ph.D dissertation monograph.—incorporated herein by reference in its entirety].

Contrary to the above discussed commercial processes, the oxidative dehydrogenation (ODH) of propane to propylene is more attractive due to its low operational cost and minimal environmental impacts. Compared to the present commercial technologies, oxidative dehydrogenation reduces costs, saves energy, and lowers greenhouse gas emissions. The most important advantage is the exothermic nature of the reaction, which requires no additional energy to accelerate the reaction. The formation of water as a byproduct of the oxidative dehydrogenation makes it possible to avoid thermodynamic constraints that are observed in the non-oxidative routes. The activity of the catalyst is also stable for a longer number of cycles due to the minimal coke deposition at the catalyst surface [E. Heracleous, M. Machli, A. A. Lemonidou, I. A. Vasalos, Oxidative dehydrogenation of dehydrogenation of ethane and propane over vanadia and molybdena supported catalysts, J. Mol. Catal. A: Chem. 232 (2005) 29-39.—incorporated herein by reference in its entirety]. It is has been thought that high propylene yield can be obtained through the ODH of propane with the successful development of efficient catalysts. In the ODH process the operation and maintenance costs are relatively low as a result of the low operating temperature. The use of a furnace and the need for decoking shutdowns are also not essential parts of the oxidative dehydrogenation process. This all accounts for comparatively small capital investment for implementation of ODH processes while still providing appreciable operational efficiencies.

The selection of a reactor is very important for the commercial scale application of oxidative dehydrogenation technology [L. Chalakov, L. K. Rihko-Struckmann, B. Munder, K. Sundmacher, Oxidative dehydrogenation of ethane in an electrochemical packed-bed membrane reactor: Model and experimental validation, Chem. Eng. J. 145 (2009) 385-392.—incorporated herein by reference in its entirety]. Fixed bed reactors are simple but difficult to maintain at isothermal conditions which can cause interference with the performance of the reactor and lead to catalyst damage and deactivation. There are numerous advantages to fluidized bed reactors over the conventional fixed reactor systems. These include controlled operation conditions at constant temperature, which assist in circumventing the issues associated with hot spots in fixed bed reactors. The absence of mass transfer limitations and uniform residence time distributions (RTDs) are also merits of fluidized bed reactors. Moreover, the ability to transport reduced catalytic species from the oxidative dehydrogenation unit to a regeneration unit is another merit of fluidized bed reactors that poses the opportunity for periodic catalyst re-oxidation. This enables twin reactor set ups, with one for oxidative dehydrogenation and the other for regeneration of the catalyst, which is important for commercial scale production [S. A. Al-Ghamdi, M. Volpe, M. M. Hossain, H. I. de Lasa, $VO_x/c-Al_2O_3$ catalyst for oxidative dehydrogenation of ethane to ethylene: desorption kinetics and catalytic activity. Appl. Catal. A: Gen. 450 (2013) 120-130; and A. W. H. Elbadawi, M. S. Ba-Shammakh, S. A. Al-Ghamdi, S. A. Razzak, M. M. Hossain, Reduction kinetics and catalytic activity of $VO_x/\gamma-Al_2O_3$—$ZrO_2$ for gas phase oxygen free ODH of ethane, Chem. Eng. J. 284 (2016) 448-457; and I. A. Bakare, M. Shamseldin, S. A. Razzak, S. A. Al-Ghamdi, M. M. Hossain (2015), H. I. de Lasa, Fluidized bed ODH of ethane to ethylene over $VO_x$—$MoO_x/\gamma-Al_2O_3$ catalyst: Desorption kinetics and catalytic activity, Chem. Eng. J. 278 (2015) 207-216.—each incorporated herein by reference in its entirety].

In addition to the proper reactor selection, the development of suitable catalysts is another key aspect for the commercial implementation of ODH processes. High yield of propylene can be obtained by employing an efficient catalyst. It has been previously reported in the literature on oxidative dehydrogenation that vanadium based catalysts offer the highest alkane conversion and alkene selectivity from ethane and other lighter hydrocarbons in the ODH reaction [M. M. Bhasin, Is true ethane oxydehydrogenation feasible, Top. Catal. 4 (2003) 145-149; and L. Capek, R. Bulanek, J. Adam, L. Smolakova, H. Sheng-Yang, P. Cicmanec, Oxidative dehydrogenation of ethane over vanadium-based hexagonal mesoporous silica catalysts, Catal. Today 141 (2009) 282-287; and L. Capek, J. Adam, T. Grygar, R. Bulanek, L. Vradman, G. Kosova-Kucerova, P. Cicmanec, P. Knotek, Oxidative dehydrogenation of ethane over vanadium supported on mesoporous materials of M41S family, Appl. Catal. A: Gen. 342 (2008) 99-106; and F. Klose, T. Wolff, H. Lorenz, A. Seidelmorgenstern, Y. Suchorski, M. Piorkowska, H. Weiss, Active species on γ-alumina-supported vanadia catalysts: Nature and reducibility J. Catal. 247 (2007) 176-193; and A. Klisinska, S. Loridant, B. Grzybowska, J. Stoch, I. Gressel, Effect of additives on properties of $V_2O_5/SiO_2$ and $V_2O_5/MgO$ catalysts II. Structure and physicochemical properties of the catalysts and their correlations with oxidative dehydrogenation of propane and ethane, Appl. Catal. A: Gen. 309 (2006) 17-27; and B. Grzybowska, A. Klisinska, K. Samson, I. Gressel, Effect of additives on properties of $V_2O_5/SiO_2$ and $V_2O_5/MgO$ catalysts: I. Oxidative dehydrogenation of propane and ethane Appl. Catal. A: Gen. 309 (2006) 10-16; and M. V. Martinez-Huerta, X. Gao, H. Tian, I. E. Wachs, J. L. G. Fierro, M. A. Banares, Oxidative dehydrogenation of ethane to ethylene over alumina-supported vanadium oxide catalysts: Relationship between molecular structures and chemical reactivity, Catal. Today 4 (2006) 279-287; and R. Grabowski, J. Sloczynski, Kinetics of oxidative dehydrogenation of propane and ethane on $VOx/SiO_2$ pure and with potassium additive, Chem. Eng. Process. 44 (2005) 1082-1093; and E. P. Reddy, R. S. Varma, Preparation, characterization, and activity of $Al_2O_3$-supported $V_2O_5$ catalysts, J. Catal. 221 (2004) 93-101; and F. Bozon-Verduraz, D. I. Enache, E. Bordes, A. Ensuque, Vanadium oxide catalysts supported on titania and zirconia: II. Selective oxidation of ethane to acetic acid and ethylene, Appl. Catal. A: Gen. 278 (2004) 103-110; and D. I. Enache, E. Bordes, A. Ensuque, F. Bozon-Verduraz, Vanadium oxide catalysts supported on zirconia and titania: I. Preparation and characterization. Appl. Catal. A: Gen. 278 (2004) 93-102; and P. Concepcion, M. T. Navarro, J. M. Lopez-Nieto, T. Blasco, B. Panzacchi, F. Rey, Vanadium oxide supported on mesoporous $Al_2O_3$: Preparation, characterization and reactivity, Catal. Today 96 (2004) 179-186; and Z. Zhao, Y. Yamada, A. Ueda, H. Sakurai, T. Kobayashi, The roles of redox and acid-base properties of silica-supported vanadia catalysts in the selective oxidation of ethane, Catal. Today 95 (2004) 163-171; and G. Busca, M. Panizza, C. Resini, F. Raccoli, R. Catani, S. Rossini, Oxidation of ethane over vanadia-alumina-based catalysts: co-feed and redox experiments, Chem. Eng. J. 93 (2003) 181-189; and A. T. Bell, E. Iglesia, M. D. Argyle, K. Chen, Ethane Oxidative Dehydrogenation Pathways on Vanadium Oxide Catalysts, J. Phys. Chem. B 106 (2002) 5421-5427; and H. I. de Lasa, M. Volpe, G. Tonetto, Butane dehydrogenation on vanadium supported catalysts under oxygen free atmosphere. Appl. Catal. A: Gen. 272 (2004) 69-78.—each incorporated herein by reference in its entirety]. This is attributed to vanadium catalysts providing lattice oxygen for the dehydrogenation of alkanes [A. T. Bell, A. Dinse, R. Schomacker, The role of lattice oxygen in the oxidative dehydrogenation of ethane on alumina-supported vanadium oxide, Phys. Chem. Chem. Phys. 29 (2009) 6119-6124; and E. A. Mamedov, V. C. Corberfin, Oxidative dehydrogenation of lower alkanes on vanadium oxide-based catalysts. The present state of the art and outlooks. Appl. Catal. A: Gen. 127 (1995) 1-40.—each incorporated herein by reference in its entirety].

The reactions involved in the oxidation of propane include the desired propane oxidative dehydrogenation to propylene as well as the combustion of propane and produced propylene to carbon (IV) oxides and carbon (II) oxide. High selectivity for propylene is thus only favorable at low propane conversions due to the lower reactivity of propane when compared to propylene. Thus, there is a need to design catalysts that will provide lattice oxygen that can selectively produce propylene from the ODH of propane while minimizing or preventing the primary and secondary combustion of propane and propylene respectively to carbon oxides [S. A. Al-Ghamdi, H. I. de Lasa, Propylene production via propane oxidative dehydrogenation over $VOx/\gamma Al_2O_3$ catalyst. Fuel 128 (2014) 120-140.—incorporated herein by reference in its entirety].

The performance of supported vanadium oxide in oxidative dehydrogenation reactions is a function of the redox properties and morphology of surface species of $VO_x$ and the acid-base character of the $VO_x$ catalyst and its support [A. Khodakov, B. Olthof, A. T. Bell, E. Iglesia, Structure and catalytic properties of supported vanadium oxides: support effects on oxidative dehydrogenation reactions. J. Catal. 181 (1999) 205-216; and M. V. Martinez-Huerta, X. Gao, H. Tian, I. E. Wachs, J. L. G. Fierro, M. A. Banares, Oxidative dehydrogenation of ethane to ethylene over alumina-supported vanadium oxide catalysts: relationship between molecular structures and chemical reactivity. Catal. Today 118 (2006) 279-287; and M. A. Banares, Supported metal oxide and other catalysts for ethane conversion: a review, Catal. Today 51 (1999) 319-348; and I. E. Wachs, B. M. Weckhuysen, Structure and reactivity of surface vanadium oxide species on oxide supports, Appl. Catal. A: Gen. 157 (1997) 67-90; and D. I. Enache, E. Bordes-Richard, F. Bozon-Verduraz, A. Ensuque, Vanadium oxide catalysts supported on zirconia and titania I. Preparation and characterization, Appl. Catal. A: Gen. 278 (2004) 93-102.—each incorporated herein by reference in its entirety]. Vanadium catalyst activity and selectivity is a function of the structure of $VO_x$ surface species. The surface density of $VO_x$ increases with vanadium loading, which is lowest for monovanadate isolated $VO_x$ species and highest for monolayer coverage species. Catalyst activity and reducibility increases as the surface density of $VO_x$ increases, while selectivity decreases as the surface density of VO$_x$ increases [J. M. Lopez-Nieto, J. Soler, P. Concepcion, J. Herguido, M. Menendez, J. Santamaria, Oxidative Dehydrogenation of Alkanes over V-based Catalysts: Influence of Redox Properties on Catalytic Performance, J. Catal. 185 (1999) 324-332; and K. Chen, A. T. Bell, E. Iglesia, The relationship between the electronic and redox properties of dispersed metal oxides and their turnover rates in oxidative dehydrogenation reactions, J. Catal. 209 (2002) 35-42; and F. Roozeboom, M. C. Mittelmeijer-Hazeleger, J. A. Moulijn, J. Medema, V. H. J. Beer De, P. J. Gellings, Vanadium oxide monolayer catalysts. 3. A Raman spectroscopic and temperature programmed reduction study of monolayer and crystal type vanadia on various supports, J. Phys. Chem. 84 (1980) 2783-2791; and J. M. Lopez-Nieto, The selective oxidative activation of light alkanes from supported vanadia to multicomponent bulk V-containing catalysts. Top Catalysis 41 (2006) 3-15; and G. Che-Galicia, R. Quintana-Solorzano, R. S. Ruiz-Martinez, J. S. Valente, C. O. C. Araiza, Kinetic modeling of the oxidative dehydrogenation of ethane to ethylene over a MoVTeNbO catalytic system, Chem. Eng. J. 252 (2014) 75-88—each incorporated herein by reference in its entirety]. Adjustments of the coordination and environment of the species of VO$_x$ can influence its catalytic behavior. The acid-base character of VO$_x$ catalyst supports has been shown in past research to have an influence on propylene selectivity in the ODH reaction. Propane adsorption and propylene desorption are functions of the acid-base properties of the support. Adsorption of the basic reactant and desorption of the acidic product are functions of the acidity of the catalyst. The acidity of the catalyst determines the protection of these chemical species from further oxidizing to carbon oxides [H. Kung, P. M. Michalakos, M. C. Kung, I. Jahan, Selectivity patterns in alkane oxidation over Mg$_3$(VO$_4$)$_2$—MgO, Mg$_2$V$_2$O$_7$, and (VO)$_2$P$_2$O$_7$. J. Catal. 140 (1993) 226-242.—incorporated herein by reference in its entirety]. The acidic character of alkanes and their corresponding olefins diminishes with increased carbon numbers and degree of molecule saturation [J. Santander, E. López, A. Diez, M. Dennehy, M. Pedernera, G. Tonetto, Ni—Nb mixed oxides: One-pot synthesis and catalytic activity for oxidative dehydrogenation of ethane, Chem. Eng. J. 255 (2014) 185-194; and J. P. Bortolozzi, T. Weiss, L. B. Gutierrez, M. A. Ulla, Comparison of Ni and Ni—Ce/Al$_2$O$_3$ catalysts in granulated and structured forms: Their possible use in the oxidative dehydrogenation of ethane reaction, Chem. Eng. J. 246 (2014) 343-352.—each incorporated herein by reference in its entirety].

There are typically strong interactions between the support (carrier) and the active site (VO$_x$). Gamma aluminum oxide (γ-Al$_2$O$_3$) is not inert towards VO$_x$. Its interactions towards a VO$_x$ phase are not weak, and hence can result in a very high dispersion of V$_2$O$_5$ on its surface. High vanadium loading can be achieved on γ-Al$_2$O$_3$, but may have lower surface areas unlike calcium oxide (CaO) which has a higher surface area. While the use of CaO may improve the resulting catalyst's superficial area and also provide the desired moderate level of acidity, it may also minimize propylene and propane combustion. Hence, the synthesis of mixed γ-Al$_2$O$_3$/CaO supports is an interesting route to examine to achieve catalyst samples with high dispersion of the surface active species and a surface area that is higher than that of γ-Al$_2$O$_3$ [N. E. Quaranta, J. Soria, V. Cortés Corbéran, J. L. G. Fierro, Selective Oxidation of Ethanol to Acetaldehyde on V$_2$O$_5$/TiO$_2$/SiO$_2$ Catalysts J. Catal. 171 (1997) 1-13.—incorporated herein by reference in its entirety].

Ahmed, et al. (U.S. Pat. No. 8,609,568B2) describes a catalyst for the ODH of propane to propylene. The disclosed catalyst obtained 5.62%, 69.68%, and 8.06% as yield of propylene, selectivity of propylene and propane conversion respectively in a fixed bed reactor over a 12.5% Ni/VMCM41 catalyst at 400° C. Brophy, et al. (EP1546072A2) describes catalytic oxidative dehydrogenation and microchannel reactors for catalytic oxidative dehydrogenation. The disclosed catalyst obtained 23%, 34.9% and 65.9% as yield of propylene, selectivity of propylene and propane conversion respectively over a Mg—Mo—V—O catalyst at 583° C. Ahmed, et al. (U.S. Pat. No. 8,623,781A1) describes the oxidative dehydrogenation of propane. The disclosed catalyst obtained 3.43%, 100%, and 3.43% as yield of propylene, selectivity of propylene and propane conversion respectively in a fixed bed reactor over a Mo$_{0.5}$V$_{0.5}$O$_{5.5}$ catalyst at 450° C.

In view of the forgoing, one aspect of the present invention is to provide fluidizable dehydrogenation catalysts comprising vanadium oxide catalytic species using a mixed γ-Al$_2$O$_3$—CaO with different CaO to γ-Al$_2$O$_3$ ratios, such as 1:1 or 1:4, as support material. The physicochemical characterization of these catalysts offers an examination of the monovanadate and polyvanadate catalytic VO$_x$ surface species, the catalyst's oxygen carrying capacity, level of acidity and active site metal-support interactions. A further aim of the present disclosure is to provide methods for producing these VO$_x$/CaO-γ-Al$_2$O$_3$ catalysts. An additional aim of the present disclosure is to provide methods for the oxidative dehydrogenation of an alkane, such as propane, to a corresponding olefin, such as propylene, employing the lattice oxygen of these VO$_x$/CaO-γ-Al$_2$O$_3$ catalysts. These methods may be performed in a gas phase oxygen free environment under fluidized bed reaction conditions while accomplishing high alkane conversion and high olefin product selectivity over CO$_x$ combustion products by appropriate control of the lattice oxygen of the catalysts.

BRIEF SUMMARY OF THE INVENTION

According to a first aspect, the present disclosure relates to a dehydrogenation catalyst comprising i) a support material comprising alumina modified by calcium oxide and ii) a catalytic material comprising one or more vanadium oxides disposed on the support material, wherein the dehydrogenation catalyst comprises 5-20% of the one or more vanadium oxides by weight relative to the total weight of the dehydrogenation catalyst.

In one embodiment, the weight ratio of calcium oxide to alumina is in the range of 1:0.2 to 1:8.

In one embodiment, the weight ratio of calcium oxide to alumina is 1:1.

In one embodiment, the one or more vanadium oxides form an amorphous phase on the surface of the support material.

In one embodiment, the one or more vanadium oxides are at least one selected from the group consisting of V$_2$O$_5$, VO$_2$, and V$_2$O$_3$.

In one embodiment, the dehydrogenation catalyst comprises at least 50% of V$_2$O$_5$ by weight relative to the total weight of the one or more vanadium oxides.

In one embodiment, the dehydrogenation catalyst has an average particle size in the range of 20-160 μm.

In one embodiment, the dehydrogenation catalyst has an apparent particle density in the range of 1-10 g/cm$^3$.

In one embodiment, the dehydrogenation catalyst has a BET surface area in the range of 5-50 m$^2$/g.

In one embodiment, the dehydrogenation catalyst is fluidizable and has Class B powder properties in accordance with Geldart particle classification.

According to a second aspect, the present disclosure relates to a method for producing the dehydrogenation catalyst of the present disclosure in any of its embodiments comprising i) mixing alumina with calcium oxide and a vanadyl coordination complex or salt in a solvent to form loaded catalyst precursors, ii) reducing the loaded catalyst precursors with $H_2$ gas to form reduced catalyst precursors, and iii) oxidizing the reduced catalyst precursors with oxygen to form the dehydrogenation catalyst.

According to a third aspect, the present disclosure relates to a method dehydrogenating an alkane to a corresponding olefin comprising flowing the alkane through a reactor comprising a catalyst chamber loaded with the dehydrogenation catalyst of the present disclosure in any of its embodiments at a temperature in the range of 400-800° C. to form the corresponding olefin and a reduced catalyst.

In one embodiment, the reactor is a fluidized bed reactor and the dehydrogenating is performed in a gas phase oxygen free environment.

In one embodiment, the alkane is propane and the corresponding olefin is propylene.

In one embodiment, the method further comprises i) oxidizing at least a portion of the reduced catalyst in a gas phase oxygen environment separated from the catalyst chamber to regenerate the dehydrogenation catalyst and ii) repeating the flowing and the oxidizing at least once with a less than 10% decrease in percent conversion of the alkane, a less than 10% decrease in selectivity for the olefin relative to a total percentage of products formed, or both.

In one embodiment, the dehydrogenation catalyst is present at an amount in the range of 0.05-1.0 g of catalyst per mL of alkane.

In one embodiment, the alkane is propane and the method has a propane conversion of 10-80% at a reaction time of 5-60 seconds and a temperature of 500-700° C.

In one embodiment, the alkane is propane and the method has a propylene selectivity of at least 60% relative to a total percentage of products formed at a reaction time of 5-60 seconds and a temperature of 500-700° C.

In one embodiment, the alkane is propane and the method has a carbon dioxide selectivity of no more than 40% relative to a total percentage of products formed at a reaction time of 5-60 seconds and a temperature of 500-700° C.

In one embodiment, the alkane is propane, the dehydrogenation catalyst has a weight ratio of calcium oxide to alumina of 1:1, and the method has a propane conversion of at least 60% and a propylene selectivity of at least 80% relative to a total percentage of products formed.

The foregoing paragraphs have been provided by way of general introduction, and are not intended to limit the scope of the following claims. The described embodiments, together with further advantages, will be best understood by reference to the following detailed description taken in conjunction with the accompanying drawings.

BRIEF DESCRIPTION OF THE DRAWINGS

A more complete appreciation of the disclosure and many of the attendant advantages thereof will be readily obtained as the same becomes better understood by reference to the following detailed description when considered in connection with the accompanying drawings, wherein.

DETAILED DESCRIPTION OF THE EMBODIMENTS

Figure 1A:
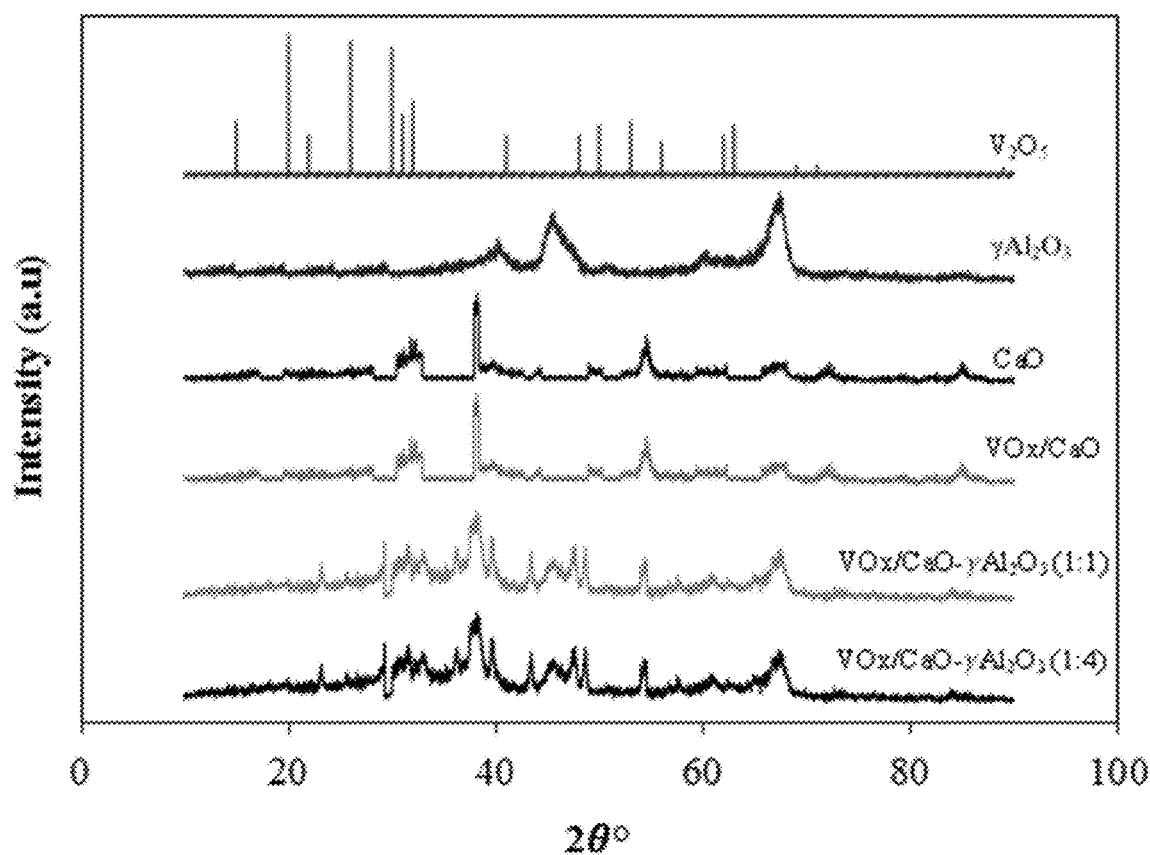
FIG. 1A is the X-ray diffraction (XRD) patterns of the three prepared catalyst samples $VO_x/CaO$-γ-$Al_2O_3$ (1:4), $VO_x/CaO$-γ-$Al_2O_3$ (1:1), and $VO_x/CaO$ as well as their components $V_2O_5$, γ-$Al_2O_3$, and CaO.

Referring now to the drawings. Embodiments of the present disclosure will now be described more fully hereinafter with reference to the accompanying drawings, in which some, but not all of the embodiments of the disclosure are shown.

According to a first aspect, the present disclosure relates to a dehydrogenation catalyst, comprising i) a support material comprising alumina modified by calcium oxide, and ii) a catalytic material comprising one or more vanadium oxides disposed on the support material, wherein the dehydrogenation catalyst comprises 5-20% of the one or more vanadium oxides by weight relative to the total weight of the dehydrogenation catalyst.

Vanadium oxide (e.g., $V_2O_5$—vanadia) is considered to be one of the most important and useful metals to be used as a catalyst due to its physical and chemical properties, and catalysis is the most dominant non-metallurgical use of vanadia. The catalytic activity of vanadia is attributed to its reducible nature and its ability to easily change its oxidation state from $V^{+3}$ to $V^{+5}$. It is generally accepted that $V^{+5}$ is the highly active initial state of the catalyst in a cycle of oxidative dehydrogenation. Vanadium oxide catalysts have been used in many industrial and lab scale catalytic reactions and processes. In many cases, vanadia catalysts are doped with promoters to improve their activity or selectivity, while various supports are used to improve mechanical strength, thermal stability, longevity, and/or catalytic performance.

As used herein, a catalyst support material refers to material, usually a solid with a high surface area, to which a catalyst is affixed. The reactivity of heterogeneous catalyst and nanomaterial based catalysts occurs at the surface atoms. Thus, great effort is made herein to maximize the surface of a catalyst by distributing it over the support. The support may be inert or participate in the catalytic reactions. The support materials used in catalyst preparation play a role in determining the physical characteristics and performance of the catalysts. Typical supports include various kinds of carbon, alumina and silica. In a preferred embodiment, the dehydrogenation catalyst of the present disclosure comprises an alumina support material, preferably a calcium oxide modified alumina support material.

As used herein, alumina refers to aluminum oxide, a chemical compound of aluminum and oxygen with the chemical formula $Al_2O_3$. Aluminum oxide is commonly called alumina and may also be referred to as aloxide, aloxite, or alundum. It is the most commonly occurring of several aluminum oxides and specifically identified as aluminum (III) oxide. It commonly occurs in its crystalline polymorphic phase $\alpha$-$Al_2O_3$ which composes the mineral corundum, the most thermodynamically stable form of aluminum oxide. $Al_2O_3$ is significant in its use to produce aluminum metals and noted for its high melting point. In one embodiment, the catalytic material is loaded on an inert alumina support. Exemplary inert alumina based inert materials include, but are not limited to aluminum oxide, alumina, alumina monohydrate, alumina trihydrate, alumina silica, bauxite, calcined aluminum hydroxides such as gibbsite, bayerite and boehmite as well as calcined hydrotalcite and the like.

In one embodiment, the alumina support material may be comprised of a plurality of different crystallographic phases. In the most common and thermodynamically stable form, corundum, the oxygen ions nearly form a hexagonal close-packed structure with aluminum ions filling two-thirds of the octahedral interstices. Each $Al^{3+}$ center is octahedral. In term of its crystallography, corundum adopts a trigonal Bravais lattice and its primitive cell contains two formula units of aluminum oxide. Aluminum oxide also exists in other phases, including the transition cubic $\gamma$ and $\eta$ phases, the monoclinic $\theta$ phase, the hexagonal $\chi$ phase, the orthorhombic $\kappa$ phase and the transition $\delta$ phase that can be tetragonal or orthorhombic. Each has unique crystal structure and properties. In the present disclosure, aluminum oxide or alumina may refer to $Al_2O_3$ having an $\alpha$ polymorph, a $\gamma$ polymorph, a $\eta$ polymorph, a $\theta$ polymorph, a $\chi$ polymorph, a $\kappa$ polymorph and a $\delta$ polymorph or mixtures thereof, preferably a $\gamma$ polymorph. In a preferred embodiment, the alumina of the present disclosure consists substantially of $\gamma$-$Al_2O_3$, preferably greater than 75% by weight relative to the total weight of alumina, preferably greater than 80%, preferably greater than 85%, preferably greater than 90%, preferably greater than 95%, preferably greater than 98%, preferably greater than 99% by weight relative to the total weight of the alumina. In at least one embodiment, the alumina support material consists essentially of $\gamma$-alumina ($\gamma$-$Al_2O_3$).

Alumina, especially $\gamma$-$Al_2O_3$ is used for its very high surface area on which active metal atoms/crystallites can spread out as reactive sites, but also for its enhancement of productivity and/or selectivity through metal-support interaction and spillover/reverse-spillover phenomena. In reactions, $\gamma$-$Al_2O_3$ must retain as much high surface area during reaction. Additives and/or modifiers and additional supports markedly increase the thermal stability of the support, effect acidity and active site metal support-interactions and prevent the loss of surface area under thermal reaction conditions.

In a preferred embodiment, the support material comprising alumina is modified by calcium oxide. As used herein, calcium oxide (CaO) also known as quicklime or burnt lime refers to a widely used chemical compound. It is a white, caustic, alkaline, crystalline solid at room temperature. The broadly used term "lime" connotes calcium containing inorganic materials, in which carbonates, oxides and hydroxides of calcium, silicon, magnesium, aluminum, and iron predominate. By contrast, "quicklime" specifically applies to the single chemical compound calcium oxide. Calcium oxide which survives processing without reacting is often termed "free lime". Quicklime is relatively inexpensive. Both it and a chemical derivative (calcium hydroxide, of which quicklime is the base anhydride) are important commodity chemicals.

In a preferred embodiment, the dehydrogenation catalyst of the present disclosure comprises 10-85% of alumina by weight relative to the total weight of the dehydrogenation catalyst, preferably 15-80%, preferably 25-75%, preferably 35-74%, preferably 45-72% of alumina by weight relative to the total weight of the dehydrogenation catalyst. In a preferred embodiment, the dehydrogenation catalyst of the present disclosure comprises 5-80% of calcium oxide by weight relative to the total weight of the dehydrogenation catalyst, preferably 10-75%, preferably 15-60%, preferably 18-46%, preferably 20-40% of calcium oxide by weight relative to the total weight of the dehydrogenation catalyst. In a preferred embodiment, the dehydrogenation catalyst of the present disclosure has a weight ratio of calcium oxide to alumina in the range of 1:0.2 to 1:8, preferably 1:0.4 to 1:7.5, preferably 1:0.5 to 1:7, preferably 1:0.6 to 1:6.5, preferably 1:0.8 to 1:6, preferably 1:0.9 to 1:5, preferably 1:1 to 1:4, preferably 1:1.5 to 1:3, preferably 1:1.75 to 1:2.5. In a more preferred embodiment, the dehydrogenation catalyst of the present disclosure has a weight ratio of calcium oxide to alumina in the range of 1:0.5 to 1:4, preferably 1:0.75 to 1:2, most preferably 1:1. In a most preferred embodiment, the dehydrogenation catalyst of the present disclosure has a weight ratio of calcium oxide to alumina of 1:1.

It is equally envisaged that the dehydrogenation catalyst of the present disclosure may be adapted to incorporate additional support materials and additional additives such as phase transformation stabilizers. In some embodiments, these additional support materials and additional additives may be used in addition to, or in lieu of alumina and/or calcium oxide. Exemplary additional support materials include, but are not limited to oxides such as, $SiO_2$, $TiO_2$, $ZrO_2$, CeO, $NbO_5$, MgO and zeolites. Exemplary additional thermal stabilizer additives include, but are not limited to, the elements La, Ce, Ba, Sr, Sm, Si, Pr and P. When lanthanum is used as an additive, the formation of lanthanum aluminate can decrease the surface energies of $\gamma$-$Al_2O_3$ lowering the driving force for sintering and stabilizing bulk phase transformation. In certain embodiments, the dehydrogenation catalyst of the present disclosure comprises less than 5% of additional additives, such as elemental lanthanum, by weight relative to the total weight of the dehydrogenation catalyst, preferably 0.1-3.0% of additional additives by weight relative to the total weight of the dehydrogenation catalyst, preferably 0.5-2.0%, preferably 0.75-1.5%, preferably 0.8-1.1%, or about 1.0% of additional additives by weight relative to the total weight of the dehydrogenation catalyst.

In a preferred embodiment, the dehydrogenation catalyst of the present disclosure comprises a catalytic material disposed on the support material, wherein the catalytic material comprises one or more vanadium oxides. As used herein, "disposed on" or "impregnated" describes being completely or partially filled throughout, saturated, permeated and/or infused. The catalytic material may be affixed on one or more surfaces of the support material the catalytic material may be affixed on an outer surface of the support material or within pore spaces of the support material. The catalytic material may be affixed to the support material in any reasonable manner, such as physisorption or chemisorption and mixtures thereof. In one embodiment, greater than 10% of the surface area (i.e. surface and pore spaces) of the support material is covered by the catalytic material, preferably greater than 15%, preferably greater than 20%, preferably greater than 25%, preferably greater than 30%, preferably greater than 35%, preferably greater than 40%, preferably greater than 45%, preferably greater than 50%, preferably greater than 55%, preferably greater than 60%, preferably greater than 65%, preferably greater than 70%, preferably greater than 75%, preferably greater than 80%, preferably greater than 85%, preferably greater than 90%, preferably greater than 95%, preferably greater than 96%, preferably greater than 97%, preferably greater than 98%, preferably greater than 99%. In preferred embodiments, the vanadium or vanadium oxide comprising catalytic material is homogeneously distributed or dispersed throughout the support material and on the surface of the support material. In preferred embodiments, this quality of the dispersion can be verified scanning electron microscopy (SEM) and/or energy dispersive X-ray analysis (EDX) providing elemental mapping, preferably vanadium elemental mapping. In other embodiments the catalytic material may form localized clusters amongst the support material, form oxide species with the support catalyst or form layers of the catalytic material and vanadium species amongst the support material, or be heterogeneously disposed on the support material and its surfaces and mixtures thereof.

In a preferred embodiment, the catalytic material comprises one or more vanadium oxides. In terms of the present disclosure, vanadium oxide may refer to vanadium (II) oxide (vanadium monoxide, VO), vanadium (III) oxide (vanadium sesquioxide or trioxide, $V_2O_3$), vanadium (IV) oxide (vanadium dioxide, $VO_2$), vanadium (V) oxide (vanadium pentoxide, $V_2O_5$). Vanadium oxide may also refer to a vanadate, a compound containing on oxoanion of vanadium generally in its highest oxidation state of $^+5$. The simplest vanadate ion is the tetrahedral orthovanadate $VO_4^{3-}$ anion. Exemplary vanadate ions include, but are not limited to, $VO_4^{3-}$, $V_2O_7^{4-}$, $V_3O_9^{3-}$, $V_4O_{12}^{4-}$, $V_5O_{14}^{3-}$ and the like. In addition to these principal oxides of vanadium, various other distinct phases exist. Phases with the general formula $V_nO_{2n+1}$, wherein n is a whole number greater than zero exist between $V_2O_5$ (vanadium (V) species) and vanadium (IV) species. Examples of these phases include $V_3O_7$, $V_4O_9$ and $V_6O_{13}$. Phases with the general formula $V_nO_{2n-1}$, wherein n is a whole number greater than zero exist between vanadium (IV) species and $V_2O_3$ (vanadium (III) species). Termed Magneli phases, they are examples of crystallographic shear compounds based on rutile structure. Examples of Magneli phases include $V_4O_7$, $V_5O_9$, $V_6O_{11}$, $V_7O_{13}$ and $V_8O_{15}$. Many vanadium oxygen phases are non-stoichiometric. In a preferred embodiment, the dehydrogenation catalyst of the present disclosure comprises 5-20% of the one or more vanadium oxides by weight relative to the total weight of the dehydrogenation catalyst, preferably 6-18%, preferably 7-16%, preferably 8-14%, preferably 9-12%, or about 10% of the one or more vanadium oxides by weight relative to the total weight of the dehydrogenation catalyst.

In a preferred embodiment, the one or more vanadium oxides are of the formula $V_xO_y$, wherein x=1-4, preferably 1-3, more preferably 1-2 and y=2-10, preferably 2-5. In a preferred embodiment, the one or more vanadium oxides are at least one selected from the group consisting of $V_2O_5$, $VO_2$ and $V_2O_3$. $V_2O_5$ or vanadium (V) oxide or vanadium pentoxide is an inorganic compound that due to its high oxidation state is both an amphoteric oxide and an oxidizing agent. $V_2O_5$ is characterized by its valuable redox properties as $V_2O_5$ is easily reduced to the stable vanadium (IV) species. In certain embodiments, the dehydrogenation catalyst comprises at least 50% of $V_2O_5$ by weight relative to the total weight of the one or more vanadium oxides, preferably greater than 60%, preferably greater than 70%, preferably greater than 80%, preferably greater than 85%, preferably greater than 90%, preferably greater than 95%, preferably greater than 96%, preferably greater than 97%, preferably greater than 98%, preferably greater than 99% of $V_2O_5$ by weight relative to the total weight of the one or more vanadium oxides, such as, for example 50-90% by weight $V_2O_5$, preferably 75-80% $V_2O_5$, more preferably 85-90%

$V_2O_5$, even more preferably at least 90-95% $V_2O_5$, most preferably 95-99.9% $V_2O_5$ relative to the total weight of the one or more vanadium oxides. In certain embodiments, the dehydrogenation catalyst of the present disclosure consists essentially of $V_2O_5$ and is substantially free of $V_2O_3$ and $VO_2$. In some embodiments, the dehydrogenation catalyst of the present disclosure is substantially free of $V_2O_3$ and comprises a mixture of at least 50% $V_2O_5$ by weight relative to the total weight of the one or more vanadium oxides, with the balance substantially comprising $VO_2$.

The different vanadia phases that can be present in supported vanadia oxide catalysts as well as the distribution among the various vanadium oxide structures can depend on the synthesis method, the vanadium precursor, solvent, calcination temperature, vanadium oxide loading, oxide support, etc. At loadings below "monolayer coverage" isolated and oligomerized surface $VO_4$ species may be present on the oxide support. The surface $VO_4$ species may possess up to three different oxygen atoms including, but not limited to, oxygen atoms forming a vanadyl group (V=O), oxygen atoms bridging two vanadia atoms (V—O—V), and oxygen atoms bridging a vanadia atom and oxide support cation (V—O-support). Depending on the vanadia surface density as well as the support material, a vanadia "monolayer coverage" may be reached. A "monolayer" refers to a single, closely packed layer of atoms or molecules, here the one or more vanadium oxides. As used herein, "monolayer coverage" refers to the completion of a 2D surface of vanadium oxide overlayer on the alumina support, and the surface becomes saturated before 3D vanadium oxide and/or $V_2O_5$ crystallites start to form and grow subsequently. In a preferred embodiment, the vanadium loading is below the monolayer coverage and the $VO_x$ species in the catalytic material are highly dispersed forming an amorphous phase on the $\gamma$-$Al_2O_3$ and CaO support surface. Alternatively, the monolayer coverage may be thought of as the minimum amount of single vanadium and/or vanadium oxide atoms or molecules to cover exactly 100% of the surface area (surface and pore spaces) of the support material uniformly. In a preferred embodiment, the monolayer coverage of the dehydrogenation catalyst of the present disclosure corresponds to 5-20 vanadium atoms per $nm^2$ of support, preferably 6-15 atoms/$nm^2$, preferably 7-10 atoms/$nm^2$, preferably 8-9 vanadium atoms per $nm^2$ of support. In certain embodiments, $V_2O_5$ crystallites may be present at vanadium oxide loadings below monolayer coverage when a precursor vanadium salt is not well dispersed over the support during synthesis or when a weak interaction exists between the vanadium oxide and the support. In one embodiment, the one or more vanadium oxides may form a crystalline phase on the surface of the lanthanum modified alumina support material, preferably a $V_2O_5$ crystalline phase. At high enough loadings, greater than monolayer coverage, vanadium oxide nanocrystals or nanoparticles having an average particle size of 1-100 nm, preferably 4-80 nm, preferably 10-60 nm, preferably 20-40 nm may be present on the surface of the catalyst support. In certain embodiments, the different surface vanadia species may be identified by techniques including, but not limited to, Raman spectroscopy, Fourier transform infrared spectroscopy (FT-IR), UV-vis spectroscopy, X-ray powder diffraction (XRD) and the like. In a preferred embodiment, the one or more vanadium oxides form an amorphous phase on the surface of the support material. Alternatively, it is envisaged that the catalytic material comprising one or more vanadium oxides of the present disclosure forms a crystalline phase on the support surface.

In other embodiments, the catalytic material may display a mixed amorphous and crystalline phase.

In certain embodiments, the catalytic material comprises one or more vanadium oxides and may optionally further comprise a promoter. As used herein, a promoter refers to an additive to improve catalyst performance. Metal promoters such as for example niobium may function to isolate active species (i.e. $VO_x$, more preferably $V_2O_5$) and to form secondary metallic oxides (i.e. $Nb_2O_5$) on support surface. Furthermore, the addition of promoters to the catalytic material blocks acid sites which decreases the total acidity of the dehydrogenation catalyst. In certain embodiments, the decrease in acidity and increase in basicity may facilitate desorption of substrates from the dehydrogenation catalyst surface, preventing further oxidation, such as, for example the undesirable combustion to carbon oxides ($CO_x$) in the oxidative dehydrogenation of light alkanes such as ethane and propane. In a preferred embodiment, the dehydrogenation catalyst of the present disclosure may further comprise 1.0-5.0% of promoter by weight relative to the total weight of the dehydrogenation catalyst, preferably 1.5-4.0%, preferably 2.0-3.75%, preferably 3.0-3.5%, or about 3.25% of promoter by weight relative to the total weight of the dehydrogenation catalyst. Exemplary promoters include, but are not limited to, metallic promoters (Nb, Cr, Mo, Ta, W), alkali promoters (Li, K, Rb) and halide promoters (Cl) and mixtures thereof. In preferred embodiments, the vanadium or vanadium oxide and promoter or promoters are homogeneously distributed throughout the catalyst support. In other embodiments the promoter may form localized clusters amongst the vanadium, form promoter oxide species with the support catalyst, form layers of promoter and vanadium species, or be disposed on the vanadium oxide species and mixtures thereof.

In a preferred embodiment, the present disclosure provides fluidizable dehydrogenation catalysts for oxidative dehydrogenation (ODH) of alkanes preferably in reactors having a fluidized bed design. As used herein "fluidizable" refers to the ability to undergo fluidization which refers to a process similar to liquefaction whereby a granular material is converted from a static solid-like to a dynamic fluid-like state. The process occurs when a fluid (liquid or gas) is passed up through the granular material. A fluidized bed is formed when a quantity of a solid particulate substance is placed under appropriate conditions to cause a solid/fluid mixture to behave as a fluid. This is usually achieved by the introduction of pressurized fluid through the particulate medium. This results in the medium then having many properties and characteristics of normal fluids, such as the ability to free flow under gravity, or to be pumped using fluid type technologies. Fluidized bed types can be broadly classified by their flow behavior including, but not limited to, stationary or bubbling fluidized beds, circulating fluidized beds (CFB), vibratory fluidized beds, transport or flash reactor (FR), and annular fluidized beds (AFB).

In certain fluidized bed reactors, the catalyst pellets lie on a grate at the bottom of the reactor. Reactants are continuously pumped into the reactor through a distributor causing the bed to become fluidized. During the fluidization, the catalyst pellets are converted from a static solid like state to a dynamic fluid like state. The bed's behavior after initial fluidization depends on the state of the reactant. If it is a liquid the bed expands uniformly with an increased upward flow of the reactant, resulting in a homogeneous fluidization. If the reactant is a gas, the bed will be non-uniform because the gas forms bubbles in the bed, resulting in aggregative fluidization. In terms of the present disclosure, the fluidization may be homogeneous or aggregative. In certain embodiments, the reactant or feed is preferably a light alkane including, but not limited to, ethane, propane and butane (including n-butane and isobutene), all of which are gases and hence, an aggregative fluidization may be probable.

Properties and parameters for determining the fluidizability, reducibility, and oxygen carrying capacity of a catalyst can be both measured and calculated. The average particle size and the particle size distribution can be measured, for example, using a Mastersizer 2000 from Malvern Instruments. For spherical or substantially spherical dehydrogenation catalyst particles, average particle size refers to the longest linear diameter of the dehydrogenation catalyst particles. In a preferred embodiment, the dehydrogenation catalyst of the present disclosure in any of its embodiments has an average particle size in the range of 20-160 μm, preferably 30-150 μm, preferably 40-120 μm, preferably 50-100 μm, more preferably 60-80 μm. In one embodiment, the particle size distribution of the dehydrogenation catalyst of the present disclosure is 10-200 μm and greater than 75% of the particles have a particle size of 40-120 μm, preferably greater than 80%, preferably greater than 85%, more preferably greater than 90% have a particle size of 40-120 μm. In another embodiment, the dehydrogenation catalyst of the present disclosure has a particle size distribution ranging from 33% of the average particle size to 133% of the average particle size, preferably 50-130%, preferably 60-125%, preferably 80-100%, preferably 90-110%, preferably 95-105% of the average particle size. In one embodiment, the dehydrogenation catalyst particles of the present disclosure are monodisperse, having a coefficient of variation or relative standard deviation, expressed as a percentage and defines as the ratio of the particle size standard deviation (σ) to the particle mean size (μ) multiplied by 100 of less than 25%, preferably less than 20%, preferably less than 15%, preferably less than 12%, preferably less than 10%, preferably less than 8%, preferably less than 6%, preferably less than 5%.

As used herein, the apparent particle density refers to the mass of the catalyst divided by the volume that it occupies. The apparent particle density can be assessed using a CREC-established method. In the method, a known amount of catalyst is introduced to a flask. The flask is filled with isopropanol and the apparent particle density (AD) is calculated using the following equation formula (I).

$$AD = \frac{W_{cat}}{V_T - V_{isopropanol}} \quad (I)$$

Where AD is the apparent particle density (g/cm$^3$), $W_{cat}$ is the catalyst weight, $V_T$ is the flask volume and $V_{isopropanol}$ is the volume of isopropanol calculated as the ratio of the weight of isopropanol needed to fill the flask and the density of isopropanol. In a preferred embodiment, the dehydrogenation catalyst of the present disclosure in any of its embodiments has an apparent particle density of 1.0-10.0 g/cm$^3$, 1.1-5.0 g/cm$^3$, preferably 1.25-4.0 g/cm$^3$, preferably 1.5-3.5 g/cm$^3$, more preferably 1.8-3.2 g/cm$^3$.

In some embodiments, with the calculated average particle size and particle apparent density values, the fluidization regime of the dehydrogenation catalyst particles of the present disclosure can be determined using Geldart's powder classification chart. Geldart groups powders into four "Geldart Groups" or "Geldart Classes". The groups are defined by solid-fluid density difference and particle size. Design methods for fluidized beds can be tailored based upon a particle's Geldart Group. For Geldart Group A the particle size is between 20 and 100 μm and the particle density is typically less than 1.4 g/cm$^3$. Prior to the initiation of a bubbling bed phase, beds from these particles will expand by a factor of 2 to 3 at incipient fluidization, due to ta decreased bulk density. Most powder-catalyzed beds utilize this group. For Geldart Group B the particle size lies between 40 and 500 μm and the particle density is between 1.4-4 g/cm$^3$. Bubbling typically forms directly at incipient fluidization. For Geldart Group C the group contains extremely fine and consequently the most cohesive particles. With a particle size of 20 to 30 μm, these particles fluidize under very difficult to achieve conditions, and may require the application of an external force, such as mechanical agitation. For Geldart Group D the particles in this regime are above 600 μm and typically have high particle densities. Fluidization of this group requires very high fluid energies and is typically associated with high levels of abrasion. Additionally, these particles are usually processed in shallow beds or in the spouting mode. The dehydrogenation catalyst of the present disclosure is preferably fluidizable and may be classified as a Geldart Group A powder, a Geldart Group B powder, a Geldart Group C powder or a Geldart Group D powder, preferably as a Geldart Group B powder. In at least one preferred embodiment, the dehydrogenation catalyst particles display a Geldart Group B powder property, which is highly fluidizable under ODH conditions. Large particles, such as those under Geldart Group D, may limit the gas phase reactant access to the inner layers of the catalyst. As a result, using smaller particles can minimize the diffusional resistance and reduction/oxidation rates can be maximized. On the other hand, very small particles, such as those under Geldart's Group C, can cause fluidization problems, channeling and loss of fines.

The Brunauer-Emmet-Teller (BET) theory aims to explain the physical adsorption of gas molecules on a solid surface and serves as the basis for an important analysis technique for the measurement of the specific surface area of a material. Specific surface area is a property of solids which is the total surface area of a material per unit of mass, solid or bulk volume, or cross sectional area. In a preferred embodiment, the dehydrogenation catalyst of the present disclosure in any of its embodiments has a BET surface area in the range of 5-50 m$^2$/g, preferably 10-45 m$^2$/g, preferably 11-40 m$^2$/g, preferably 12-30 m$^2$/g/preferably 13-28 m$^2$/g, preferably 14-25 m$^2$/g.

The catalytic activity of many oxides in various processes is due to their Lewis and Bronsted acidities. In addition to effects on surface area, catalyst modifications (i.e. the modification of alumina with CaO) may also decrease the surface acidity and metal-support interactions of the catalyst, thereby enhancing olefin selectivity in oxidative dehydrogenation reactions and reducing coke (CO$_x$) formation. The catalyst acidity plays a role in metal support interactions that affect VO$_x$ reducibility. The reducibility may impact catalyst activity and selectivity by providing O$_2$ for oxidation and high acidity not favoring selective oxidation. A number of techniques have been developed for the characterization of acid-base surface properties of catalysts. The adsorption of volatile amines including, but not limited to, ammonia (NH$_3$), pyridine (C$_5$H$_5$N), n-butylamine (CH$_3$CH$_2$CH$_2$CH$_2$NH$_2$), quinolone (C$_9$H$_7$N) and the like is often used to determine the acid site concentration of solid catalysts. The amount of the base remaining on the surface after evacuation is considered chemisorbed and serves as a measure of the acid site concentration. The adsorbed base concentration as a function of evacuation temperature can give a site strength distribution. Another means of determining the site strength distribution is calorimetry or the temperature-programmed desorption (TPD).

Ammonia or $NH_3$-TPD experiments are used to determine the total acidity of the catalyst. TPD can further give an idea about metal-support interactions by modeling $NH_3$ desorption kinetics and be used to determine the strength of acid sites available on the catalyst surface. In a preferred embodiment, the dehydrogenation catalyst of the present disclosure in any of its embodiments has a total acidity in the range of 0.1-5.0 mmol of $NH_3$ per gram of catalyst, preferably 0.2-4.0 mmol of $NH_3$ per gram of catalyst, preferably 0.3-3.0 mmol of $NH_3$ per gram of catalyst, preferably 0.4-2.8 mmol of $NH_3$ per gram of catalyst, preferably 0.5-2.5 mmol of $NH_3$ per gram of catalyst when measured with a heating rate of 5-20° C./min, preferably 10-15° C./min. In a preferred embodiment, the dehydrogenation catalyst of the present disclosure has a lower acidity than pure alumina. In a preferred embodiment, the dehydrogenation catalyst of the present disclosure has an energy of $NH_3$ desorption established by $NH_3$-TPD kinetic analysis and an indicator of active site metal-support interactions in the range of 10-100 kJ/mol, preferably 25-75 kJ/mol, preferably 30-60 kJ/mol, preferably 35-50 kJ/mol. In one embodiment, the inclusion of greater amounts of CaO to the support material comprising alumina modified by calcium oxide may decrease the total acidity of the dehydrogenation catalyst of the present disclosure, increase the oxygen carrying capacity of the dehydrogenation catalyst of the present disclosure and decrease the activation energy of ammonia desorption of the dehydrogenation catalyst of the present disclosure relative to a substantially similar catalyst lacking CaO modified support material or comprising a lower weight ratio of calcium oxide to alumina. In addition, the effects of intermediate catalyst acidity, moderate active site metal-support interactions and moderate active site metal-support interactions may favor product selectivity in oxidative dehydrogenation reactions.

According to a second aspect, the present disclosure relates to a method for producing the dehydrogenation catalyst of the present disclosure in any of its embodiments, comprising i) mixing alumina with calcium oxide and a vanadyl coordination complex or salt in a solvent to form loaded catalyst precursors, ii) reducing the loaded catalyst precursors with $H_2$ gas to form reduced catalyst precursors, and iii) oxidizing the reduced catalyst precursors with oxygen to form the dehydrogenation catalyst.

Two main methods are typically used to prepare supported catalysts. In the impregnation method, the solid support or a suspension of the solid support is treated with a solution of a precatalyst (for instance a metal salt or metal coordination complex), and the resulting material then activated under conditions that will convert the precatalyst to a more active state, such as the metal itself or metal oxides of the metal. In such cases, the catalyst support is usually in the form of pellets or spheres. Alternatively, supported catalysts can be prepared from homogenous solution by co-precipitation. In terms of the present disclosure, it is envisaged that the dehydrogenation catalyst may be formed by an impregnation method or a co-precipitation method, preferably by an impregnation method, preferably by an impregnation method through soaking with an excess solvent. Supports are usually thermally very stable and withstand processes required to activate precatalysts. For example, many pre-catalysts are activated by exposure to a stream of hydrogen or air (oxygen) at high temperatures, additionally many precatalysts may be activated and/or reactivated by oxidation-reduction cycles, again at high temperatures.

In one step of the process, alumina is mixed with calcium oxide and a vanadyl coordination complex or salt in a solvent to form loaded catalyst precursors. In one embodiment, the unmodified alumina and calcium oxide supports before metal loading may be optionally initially dried and/or calcined to remove moisture and other volatile compounds. In one embodiment, the preemptive calcining may be performed at a temperature of 300-600° C., preferably 400-550° C., or about 550° C. for a period of up to 8 hours, preferably up to 6 hours, preferably up to 4 hours, or about 4 hour. The precalcining may be performed at a temperature of 600-800° C., preferably 650-750° C., or about 725° C. for a period of up to 8 hours, preferably up to 6 hours, or about 4 hours.

The manner in which the vanadium oxide is deposited onto a support can have an influence on the properties of the active component in the final catalyst. Typically the main method of dispersing vanadium oxide on support materials is the classic incipient wetness impregnation method in a solvent where the vanadium salt is soluble. The impregnation method is performed by contacting the support with a certain volume of solution containing the dissolved vanadium oxide precursor. If the volume of the solution is either equal to or less than the pore volume of the support, the technique is referred to as incipient wetness. This particular synthesis route can show a broad variation of vanadium oxide surface species at all loadings, particularly loadings below monolayer coverage, depending on the synthesis conditions. In one embodiment, this method may lead to the formation of three-dimensional $V_2O_5$ nanoparticles, even at low vanadium oxide loadings. In another embodiment, this method may lead to the formation of an amorphous vanadium oxide phase on the surface of the support.

In a preferred embodiment, the loaded catalyst precursors are prepared by an incipient wetness method of impregnation. The alumina support can be immersed in a solution comprising calcium oxide and vanadium and/or a vanadium salt or coordination complex. In one embodiment, the vanadium salt or coordination complex may be a vanadium (IV), vanadium (V) or vanadium (III) salt. Exemplary vanadium salts or coordination complexes include, but are not limited to, ammonium metavanadate in mixtures of water and oxalic acid or methanol and oxalic acid, vanadium (III) acetylacetonate $(V(AcAc)_3)$ or vanadyl acetylacetonate $(VO(AcAc)_2)$ in toluene, $VO(iPrO)_3$, $VO(OC_2H_5)_3$, or $VO(OC_2H_7)_3$ in 2-propanol, as well as vanadyl sulfate, vanadium pentoxide, vanadium (III) chloride, vanadium oxytripropoxide, tetrakis(diethylamido)vanadium (IV), vanadium (IV) chloride, vanadium (III) chloride tetrahydrofuran complex, vanadium (V) oxychloride, vanadium (V) oxyfluoride, and the like. Preferably, the vanadium salt or coordination complex is vanadium (III) acetylacetonate $(V(AcAc)_3)$ or vanadyl acetylacetonate $(VO(AcAc)_2)$, most preferably vanadyl acetylacetonate $(VO(AcAc)_2)$. The vanadium salt is preferably phosphorous free. In a preferred embodiment, the solvent is a polar protic solvent. Exemplary polar protic solvents include, but are not limited to, formic acid, n-butanol, isopropanol, n-propanol, ethanol, methanol, acetic acid, water and mixtures thereof, preferably the solvent is ethanol. It is equally envisaged that the present method may be adapted to incorporate non-polar solvents including, but not limited to, pentane, cyclopentane, hexane, cyclohexane, benzene, toluene, 1,4-dioxane, chloroform, diethyl ether and dichloromethane, as well polar aprotic solvents including, but not limited to, tetrahydrofuran, ethyl acetate, acetone, dimethylformamide, acetonitrile, dimethyl sulfoxide, nitromethane, propylene carbonate and mixtures thereof.

In a preferred embodiment the vanadium salt is vanadyl acetylacetonate $VO(AcAc)_2$ and the solvent is ethanol. In a preferred embodiment the solution has a vanadium concentration of 0.01-1.0 M, preferably 0.05-0.5 M, preferably 0.1-0.25 M, preferably 0.125-0.2 M, or about 0.15 M. In a preferred embodiment, the mixing of the alumina support material with the calcium oxide and vanadyl coordination complex or salt in a solvent is performed at a temperature of 20-40° C., preferably 20-30° C., or about 25° C. for a period of less than 48 hours, preferably less than 36 hours, preferably less than 24 hours, preferably less than 18 hours, preferably less than 12 hours, preferably less than 10 hours and optionally with stirring and/or ultrasonication for 1-60 minutes, preferably 5-30 minutes, preferably 10-20 minutes to achieve a homogeneous mixture. After mixing the solution can be filtered and separated from the solvent to provided loaded catalyst precursors.

In another embodiment, it is equally envisaged that the method may be adapted to other means of dispersing and depositing the vanadium oxide on the support material. Both adsorption from solution (i.e. grafting) based on attaching vanadia from the solution through reaction with hydroxyl groups on the surface of the support and ion exchange methods permitting the ionic vanadium oxide species present in an aqueous solution to be electrostatically attracted by charged sites of the support surface have been used. Exemplary other means include, but are not limited to, vapor-fed flame synthesis, flame spray pyrolysis, sputter deposition, atomic layer deposition and chemical vapor deposition (CVD). For example, chemical vapor deposition (CVD) uses volatile molecular metal precursors (i.e. $O{=}VCl_3$, $O{=}V(OC_2H_5)_3$ or $O{\uparrow}V(OiPr)_3$) to modify oxide support surface and provide a way to control the dispersion of the active sites.

In certain embodiments, in addition to the methods employed to disperse vanadium oxide material on different supports, the drying and/or calcination used for the fixation of the vanadia may be a crucial step of the catalyst preparation due to the conversion of the initial vanadium species that may result in a broad variety of $V_xO_y$ species from a nominally simple impregnation process. At high calcination temperatures, mixed oxide compounds or solid solutions can be formed with some oxide supports (i.e. $AlVO_4$). In a preferred embodiment, the loaded catalyst supports are dried before the reduction and the oxidation at room temperature and following natural drying before the reduction and the oxidation at a temperature of up to 300° C., preferably up to 250° C., preferably up to 200° C., preferably up to 175° C., preferably up to 150° C., preferably up to 125° C., preferably up to 100° C. for a period of up to 60 hours, preferably up to 48 hours, preferably up to 36 hours, preferably up to 24 hours, preferably up to 12 hours.

In one step of the process the loaded catalyst precursors are reduced with $H_2$ gas to form reduced catalyst precursors. As used herein, reduction refers to the gain of electrons or a decrease in oxidation state by a molecule, atom or ion. In a preferred embodiment, the loaded catalyst precursors are reduced under a flow of hydrogen gas comprising 1-40% $H_2$, preferably 2-20% $H_2$, preferably 4-18% $H_2$, preferably 6-16% $H_2$, preferably 8-14% $H_2$, or about 10% $H_2$ as a molar percentage and 60-99% inert gas, preferably 70-95% inert gas, preferably 80-94% inert gas, preferably 85-92% inert gas, or about 90% inert gas as a molar percentage. Exemplary inert gases include nitrogen ($N_2$) and argon (Ar), preferably argon. In a preferred embodiment, the reduction under hydrogen gas flow is performed at a temperature of 300-800° C., preferably 350-750° C., preferably 400-700° C., preferably 425-650° C., preferably 450-600° C., preferably 475-550° C., or about 500° C. for a period of 1-18 hours, preferably 2-12 hours, preferably 4-8 hours, or about 6 hours. In certain embodiments, the reduction of the loaded catalyst precursors may be performed in a fluidized bed reactor.

In one step of the process the reduced catalyst precursors are oxidized with oxygen to form the dehydrogenation catalyst of the present disclosure in any of its embodiments. As used herein, oxidation refers to the loss of electrons or an increase in oxidation state by a molecule, atom or ion. Oxidation reactions are commonly associated with the formation of oxides from oxygen molecules. Oxygen itself is the most versatile oxidizer. In a preferred embodiment, the reduced catalyst precursors are oxidized under air flow comprising 20-25% $O_2$, preferably 20.5-22% $O_2$, or about 21% $O_2$ as a molar percentage and 75-80% $N_2$, preferably 77-79% $N_2$, or about 78% $N_2$ as a molar percentage. In a preferred embodiment, the oxidation under air flow or calcination under air flow is performed at a temperature of 300-700° C., preferably 350-650° C., preferably 400-600° C., preferably 425-575° C., preferably 450-550° C., preferably 475-525° C., or about 500° C. for a period of time of 1-12 hours, preferably 2-8 hours, preferably 3-6 hours, or about 4-5 hours. In certain embodiments, obtaining the oxide catalyst form will be accompanied by a characteristic yellow color or color change indicating the presence of $V_2O_5$ on the support surface.

According to a third aspect, the present disclosure relates to a method for dehydrogenating an alkane to a corresponding olefin comprising flowing the alkane through a reactor comprising a catalyst chamber loaded with the dehydrogenation catalyst of the present disclosure in any of its embodiments at a temperature in the range of 400-800° C. to form the corresponding olefin and a reduced catalyst.

The general nature of the alkane substrate is not viewed as particularly limiting to the oxidative dehydrogenation described herein. As used herein, "alkane" or "paraffin" unless otherwise specified refers to both branched and straight chain saturated primary, secondary and/or tertiary hydrocarbons of typically $C_1$-$C_{10}$. It is equally envisaged that the present disclosure may be adapted to cycloalkanes referring to cyclized alkanes containing one or more rings and substituted alkanes and/or substituted cycloalkanes referring to at least one hydrogen atom that is replaced with a non-hydrogen group, provided that normal valencies are maintained and that the substitution results in a stable compound. In a preferred embodiment, the alkane is at least one straight-chain linear alkane of $C_1$ to $C_{10}$, preferably $C_2$-$C_6$, more preferably $C_2$-$C_4$ selected from the group consisting of ethane ($C_2H_6$), propane ($C_3H_8$), and a butane ($C_4H_{10}$, n-butane, isobutane) and the corresponding olefin is a light olefin selected from the group consisting of ethylene, propylene, a butene (1-butene, (Z)-but-2-ene, (E)-but-2-ene, isobutylene (2-methylpropene)) and butadiene respectively, more preferably the alkane is ethane or propane and the corresponding olefin is ethylene or propylene respectively, most preferably the alkane is propane and the corresponding olefin is propylene. In certain embodiments, the alkane may be sourced from other industrial processes such as those used in the petrochemical industry. Feedstocks generated from petroleum including, but not limited to, ethane, propane, butane, naphtha, pet naphtha, pygas, light pygas, and gas oil may serve as substrates for the method of dehydrogenating an alkane described herein. In some embodiments, these streams or feedstocks may be processed (i.e. hydroprocessed) prior to the dehydrogenation. In certain embodiments, the alkane may be propane and the propane may be abundantly available from a natural gas source or a refinery off gas source.

As used herein, dehydrogenation refers to a chemical reaction that involves the removal of hydrogen from a molecule. It is the reverse process of hydrogenation. The dehydrogenation reaction may be conducted on both industrial and laboratory scales. Essentially dehydrogenation converts saturated materials to unsaturated materials and dehydrogenation processes are used extensively in fine chemicals, oleochemicals, petrochemicals and detergents industries. The most relevant industrial pathway in light olefin production is typically steam cracking; the alternative fluid catalytic cracking (FCC) is only able to produce desired olefins in small concentrations with significant catalyst deactivation. The FCC catalytic dehydrogenation of alkanes is more selective but the reaction characteristics pose inherent difficulties and impose certain technical constraints. For example, thermal dehydrogenation is strongly endothermic and often requires operation at both high temperature and high alkane partial pressure. The oxidative dehydrogenation (ODH) of an alkane, which couples the endothermic dehydrogenation of the alkane with the strongly exothermic oxidation of hydrogen avoids the need for excess internal heat input and consumes hydrogen. The advantages of the alkane ODH reaction include that the reaction is i) exothermic, ii) thermodynamically unrestricted, iii) operates at a much lower temperature, and iv) minimizes coke ($CO_x$) deposition ensuring long-term stability of the catalyst.

Under standard operating conditions, an alkane is converted to a corresponding olefin by oxidative dehydrogenation in the presence of the dehydrogenation catalyst described herein in accordance with the chemical equation represented by formula (II), wherein y is a positive whole number, preferably y is 2, 3, or 4, more preferably y is 3 and the alkane converted is propane and the corresponding olefin is propylene.

$$C_yH_{2y+2} + \tfrac{1}{2}V_2O_5 \rightarrow C_yH_{2y} + H_2O + \tfrac{1}{2}V_2O_3 \qquad (II)$$

In some embodiments the alkane to olefin conversion may be accompanied by complete oxidation of the alkane or the olefin as side and/or secondary reactions as represented in formula (III) and formula (IV), wherein y is a positive whole number, preferably y is 2, 3, or 4, more preferably y is 3, and y is the sum of a and b (y=a+b). The yield of alkenes or olefins obtained by oxidative dehydrogenation on catalysts is limited by alkene or alkane combustion to carbon oxides $CO_x$ (i.e. CO and $CO_2$). In some embodiments a=y and b=0 and $CO_2$ is the sole combustion product considered. The minimization of these undesirable consecutive and/or parallel combustion reactions is a key in the development of successful oxidative dehydrogenation catalysts.

$$C_yH_{2y+2} + \tfrac{1}{2}V_2O_5 \rightarrow aCO_2 + bCO + \tfrac{(2y+2)}{2}H_2O + \tfrac{1}{2}V_2O_3 \qquad (III)$$

$$C_yH_{2y} + \tfrac{1}{2}V_2O_5 \rightarrow aCO_2 + bCO + \tfrac{2y}{2}H_2O + \tfrac{1}{2}V_2O_3 \qquad (IV)$$

The performance of the oxidative dehydrogenation can be modulated by adjusting conditions including, but not limited to, temperature, pressure, reaction time and/or catalyst loading. One important objective in developing oxidative dehydrogenation catalysts is to reduce the reaction temperature of the process to minimize energy consumption. In a preferred embodiment, the oxidative dehydrogenation of an alkane to a corresponding olefin is carried out a temperature in the range of 400-800° C., preferably 450-750° C., preferably 500-700° C., preferably 525-675° C., preferably 540-660° C., preferably 560-640° C., preferably 580-620° C., or about 640° C. and preferably at approximately standard pressure (100 kPa, 1 bar, 14.5 psi, 0.9869 atm) such as for example 10-20 psi, preferably 12-18 psi, preferably 14-16 psi, preferably 14.25-15 psi, or approximately 14.4-14.8 psi. In a preferred embodiment, the catalyst-alkane feed contact time is in the range of 5-60 seconds, preferably 10-40 seconds, preferably 15-35 seconds, more preferably 16-30 seconds, or about 17 seconds. In a preferred embodiment, the catalyst loading or amount of catalyst present in the oxidative dehydrogenation reaction is in the range of 0.05-1.0 g of catalyst per mL of alkane feed injected, preferably 0.10-0.80 g/mL, preferably 0.15-0.60 g/mL, preferably 0.20-0.50 g/mL, preferably 0.25-0.45 g of catalyst per mL of alkane feed injected, or about 0.42 g/mL. The conditions may vary from these ranges and still provide acceptable conditions for performing the oxidative dehydrogenation of an alkane to a corresponding olefin utilizing the dehydrogenation catalyst of the present disclosure.

Oxidative dehydrogenation catalysts are evaluated for their percent conversion of the alkane as well as their selectivity to a product (i.e. the corresponding olefin or $CO_x$ (CO and/or $CO_2$). The definitions used in calculating the conversion and selectivity are represented for the method of the present disclosure using the oxidative dehydrogenation catalyst are represented in formula (V) and formula (VI) respectively.

$$\text{Alkane conversion, } X_{alkane}(\%) = \frac{\sum_j z_j n_j}{(y)n_{alkane} + \sum_j z_j n_j} \times 100 \qquad (V)$$

$$\text{Selectivity to a product, } S_j(\%) = \frac{z_j n_j}{\sum_j z_j n_j} \times 100 \qquad (VI)$$

In these formulas, $z_j$ and $n_j$ are the number of atoms of carbon and moles of gaseous carbon containing product j, respectively. The term $n_{alkane}$ is the mole of unconverted alkane in the product stream (i.e. y=3 for propane, y=2 for ethane, etc.). Alternatively, the conversion of alkane (%) can be thought of as moles of alkane converted divided by moles of alkane fed multiplied by 100% and the selectivity to product can be thought of as moles of product divided by the difference of moles of alkane reacted minus moles of product multiplied by 100%.

In one embodiment, the method of the present disclosure has an oxidative dehydrogenation alkane conversion rate as defined with formula (V) of up to 80%, preferably up to 70%, preferably up to 65%, preferably up to 60%, preferably up to 55%, preferably up to 50%, preferably up to 45%, preferably up to 40%, preferably up to 35%, such as for example 10-80%, preferably 20-70%, preferably 25-65%, more preferably 30-60% and at least 5%, preferably at least 10%, preferably at least 15%, preferably at least 20%, preferably at least 25%. In another embodiment, the alkane is ethane, propane, or butane and the method has an alkane conversion of up to 80%, preferably up to 70%, preferably up to 65%, preferably up to 60%, preferably up to 55%, preferably up to 50%, preferably up to 45%, preferably up to 40%, preferably up to 35%, such as for example 5-50%, preferably 10-45%, preferably 12-40%, more preferably 15-35%. In a preferred embodiment, the alkane is propane and the corresponding olefin is propylene and the method is performed with a catalyst-alkane feed contact time or reaction time of 5-60 seconds, preferably 10-40 seconds, preferably 15-35 seconds, more preferably 16-30 seconds at a reaction dehydrogenation temperature of 500-700° C., preferably 525-675° C., preferably 540-660° C., preferably 560-640° C. and the method has a propane conversion of 10-80%, preferably 20-70%, preferably 30-65%, preferably 40-60%.

In one embodiment, the method of the present disclosure has an oxidative dehydrogenation olefin selectivity relative to a total percentage of products formed as defined with formula (VI) of at least 60%, preferably at least 65%, preferably at least 70%, preferably at least 75%, preferably at least 80%, preferably at least 85%, preferably at least 90%, preferably at least 95% such as for example 60-90%, preferably 65-88%, preferably 70-86%, more preferably 75-85%. In another embodiment, the alkane is ethane, propane, or butane and the method has an olefin selectivity relative to a total percentage of products formed of at least 60%, preferably at least 65%, preferably at least 70%, preferably at least 75%, preferably at least 80%, preferably at least 85%, preferably at least 90%, preferably at least 95% such as for example 60-90%, preferably 65-89%, preferably 70-88%, more preferably 75-86%. In a preferred embodiment, the alkane is propane and the corresponding olefin is propylene and the method is performed with a catalyst-alkane feed contact time or reaction time of 5-60 seconds, preferably 10-40 seconds, preferably 15-35 seconds, more preferably 16-30 seconds at a reaction dehydrogenation temperature of 500-700° C., preferably 525-675° C., preferably 540-660° C., preferably 560-640° C. and the method has a propylene selectivity relative to a total percentage of products formed of at least 60%, preferably at least 65%, preferably at least 70%, preferably at least 75%, preferably at least 80%, preferably at least 85%, preferably at least 90%, preferably at least 95% such as for example 60-95%, preferably 65-90%, preferably 70-88%, more preferably 75-86%.

In a preferred embodiment, the method of the present disclosure is performed with a catalyst-alkane feed contact time or reaction time of 5-60 seconds, preferably 10-40 seconds, preferably 15-35 seconds, more preferably 16-30 seconds at a reaction dehydrogenation temperature of 500-700° C., preferably 525-675° C., preferably 540-660° C., preferably 560-640° C. and the method has a $CO_2$ or complete combustion selectivity relative to a total percentage of products formed that is less than the olefin selectivity, and the $CO_2$ selectivity is no more than 40%, preferably no more than 35%, preferably no more than 30%, preferably no more than 25%, preferably no more than 20%, preferably no more than 15%, preferably no more than 10% such as for example 5-40%, preferably 10-35%, preferably 20-30%. In a preferred embodiment, the method of the present disclosure has a CO selectivity relative to a total percentage of products formed that is less than the olefin selectivity and less than the $CO_2$ selectivity and the CO selectivity is no more than 38%, preferably no more than 35%, preferably no more than 30%, preferably no more than 25%, preferably no more than 20%, preferably no more than 15%, preferably no more than 10% such as for example 5-40%, preferably 10-35%, preferably 20-30%.

In a more preferred embodiment, the alkane is propane and the corresponding olefin is propylene and the dehydrogenation catalyst of the present disclosure in any of its embodiments has a weight ratio of calcium oxide to alumina in the range of 1:0.5 to 1:4, preferably 1:0.75 to 1:2, most preferably 1:1 and the method of the present disclosure is performed with a catalyst-alkane feed contact time or reaction time of 5-60 seconds, preferably 10-40 seconds, preferably 15-35 seconds, more preferably 16-30 seconds at a reaction dehydrogenation temperature of 500-700° C., preferably 525-675° C., preferably 540-660° C., preferably 560-640° C. and the method has a propane conversion of at least 60%, preferably at least 62%, preferably at least 64%, preferably at least 65%, preferably at least 66%, preferably at least 68%, preferably at least 70%, preferably at least 75%, preferably at least 80%, preferably at least 85%, preferably at least 90% and a propylene selectivity relative to a total percentage of products formed of at least 80%, preferably at least 82%, preferably at least 84%, preferably at least 85%, preferably at least 86%, preferably at least 88%, preferably at least 90%, preferably at least 95%.

In a preferred embodiment, the method of the present disclosure and alkane oxidative dehydrogenation (ODH) reactions incorporating the dehydrogenation catalyst described herein are performed in a gas phase oxygen-free environment or atmosphere. The presence of excess oxygen inside the reactor or catalyst chamber increases the combustion reaction and therefore $CO_x$ production. Preferably, the amount of oxygen available for the reaction is controlled by the catalyst available, or lattice oxygen of the catalyst, specifically the vanadium oxide species. By this method, in reducing the catalyst loading or increasing the alkane feed to catalyst ratio one can further minimize the available oxygen and decrease the combustion reaction, thus enhancing olefin selectivity.

In a preferred embodiment, the reactor is a fluidized bed reactor. As used herein, a fluidized bed reactor (FBR) is a type of reactor device that can be used to carry out a variety of multiphase chemical reactions. In this type of reactor, a fluid (gas or liquid) is passed through a granular solid material (usually a catalyst, preferably spherically shaped) at high enough velocities to suspend the solid and cause it to behave as though it were a fluid. This process, known as fluidization, imparts many important advantages to the fluidized bed reactor. It is equally envisaged that the method of the present disclosure may be adapted to be performed in a fixed-bed reactor, but this generally results in lower oxidative dehydrogenation catalyst activity.

The solid substrate (the catalytic material upon which the chemical species react) material in a fluidized bed reactor is typically supported by a porous plate known as a distributor, distributor plate or sparger distributor. The fluid is then forced through the distributor up through the solid material. At lower fluid velocities, the solids remain in place as the fluid passes through the voids in the material. This is referred to as a packed bed reactor. As the fluid velocity is increased, the reactor will reach a stage where the force of the fluid on the solids is enough to balance the weight of the solid material. This stage is referred to as incipient fluidization and occurs at this minimum fluidization velocity. Once this minimum velocity is surpassed, the contents of the reactor bed begin to expand and swirl around similar to an agitated tank or boiling pot of water. The reactor is now a fluidized bed. Depending on the operating conditions and properties of the solid phase various flow regimes can be observed in this type of reactor.

The fluidized bed reactor technology has many advantages including, but not limited to, uniform particle mixing, uniform temperature gradients and the ability to operate the reactor in continuous state. Due to the intrinsic fluid-like behavior of the solid material, fluidized beds do not experience poor mixing as in packed beds. The complete mixing allows for a uniform product that can often be hard to achieve in other reaction designs. The elimination of radial and axial concentration gradients also allows for better fluid-solid contact, which is essential for reaction efficiency and quality. Many chemical reactions require the addition or removal of heat. Local hot or cold spots within the reaction bed, often a problem in packed beds, are avoided in fluidized conditions such as the fluidized bed reactor. In other reactor types, these local temperature differences, especially hot spots, can result in product degradation. Thus fluidized bed reactors are well suited to exothermic reactions. The bed-to-surface heat transfer coefficients for fluidized bed reactors are also high. The fluidized bed nature of these reactors allows for the ability to continuously withdraw product and introduce new reactants into the reaction vessel. Operating at a continuous process state allows for the more efficient production and removes startup conditions in batch processes.

In certain embodiments, the fluidizability, reactivity, and stability of the catalyst of the present disclosure or experimental laboratory scale oxidative dehydrogenation reactions and/or reaction behaviors may be demonstrated or evaluated in a Plexiglas unit with dimensions matching that of a CREC riser simulator. This type of reactor has a capacity of 50-60 $cm^3$, preferably 51-55 $cm^3$ or about 53 $cm^3$ and is a batch unit designed for catalyst evaluation and kinetic studies under fluidized bed reactor conditions. The major components of the CREC riser simulator include, but are not limited to, a vacuum box, a series of sampling valves, a timer, two pressure transducers and three temperature controllers. The product gas may be analyzed by gas chromatography (GC) with a thermal conductivity detector (TCD) and flame ionization detector (FID).

The oxidative dehydrogenation method of the present disclosure may be performed at various temperatures and contact times. In one embodiment, the contact times may be chosen to be consistent with catalyst reduction temperature reported by temperature programmed reduction (TPR) analysis. In a typical procedure, the oxidized catalyst sample of the present disclosure is loaded into the reactor basket and the reactor basket is checked for potential leaks. Following the leak test the system is purged by flowing pure inert gas, preferably nitrogen or argon, most preferably argon. The temperature program is started to heat the reactor to the desired temperature. The inert gas flow is maintained to keep the reactor from any interference of gas phase oxygen. Once the reactor reaches a desired temperature, the inert gas flow is discontinued and the reactor isolation valve is closed once a desired pressure level is reached. A vacuum pump may be used to evacuate the vacuum box down to less than 100 kPa, preferably less than 50 kPa, preferably less than 25 kPa, preferably less than 20 kPa. In one embodiment, the catalyst may be fluidized by rotating agitation, preferably by an impeller at a speed of 100-5000 rpm, preferably 1000-4500 rpm, preferably 2000-4250 rpm, preferably 3000-4000 rpm. In another embodiment, no agitation (i.e. 0 rpm) is necessary to fluidize the catalyst. The alkane feed is injected into the reactor using a preloaded gas tight syringe and the reaction proceeds for a pre-specified amount of time. At the termination point, the isolation valve between the reactor and vacuum box may automatically open and transfer all reactant and products to the vacuum box for analysis.

In a preferred embodiment, the method for the dehydrogenation of an alkane to a corresponding olefin utilizing the dehydrogenation catalyst of the present disclosure in any of its embodiments further comprises i) oxidizing at least a portion of the reduced catalyst in an oxygen environment separated from the catalyst chamber to regenerate the dehydrogenation catalyst of the present disclosure and ii) repeating the flowing and the oxidizing at least once with a less than 10% decrease in percent conversion of the alkane, a less than 10% decrease in selectivity for the olefin relative to a total percentage of products formed, or both. In this manner, the dehydrogenation catalyst can be recovered and reused in at least 2 reaction iterations, preferably at least 3, preferably at least 4, preferably at least 5, preferably at least 6, preferably at least 10, preferably at least 15, preferably at least 20 reaction iterations.

The dehydrogenation catalyst of the present disclosure can be reformed or regenerated from the reduced catalyst; in this case the regeneration is the oxidation of the reduced vanadium species on the support surface. In a preferred embodiment, the regeneration is oxidation under air flow of the reduced catalyst and is performed at a temperature of up to 700° C., preferably up to 600° C., preferably up to 500° C., preferably up to 400° C. for a period of time of up to 30 minutes, preferably up to 20 minutes, preferably up to 15 minutes, preferably up to 10 minutes, preferably up to 5 minutes. In one embodiment, the reduced catalyst can flow out of the catalyst chamber to an additional chamber or re-oxidation chamber, be exposed to air flow to regenerate the dehydrogenation catalyst, and flow back to catalyst chamber for use in subsequent reaction iterations. In a preferred embodiment, catalyst performance remains stable in cycles in terms of alkane conversion and olefin selectivity indicating the catalyst's ability to be regenerated which confirms catalyst stability at high temperatures. In a preferred embodiment, at least a portion of the reduced catalyst is oxidized to regenerate the dehydrogenation catalyst per reaction cycle, preferably less than 60%, preferably less than 40%, preferably less than 30%, preferably less than 20%, preferably less than 15%, preferably less than 10%, preferably less than 8% of the reduced catalyst is oxidized to regenerate the dehydrogenation catalyst per reaction cycle.

In a preferred embodiment, there is a less than a 10% change in percent alkane conversion between the first and second iteration, preferably less than 5%, preferably less than 4%, preferably less than 3%, preferably less than 2%, preferably less than a 1% change in percent alkane conversion between the first and second iteration. In another embodiment, there is a less than a 20% change in percent alkane conversion, preferably less than 15%, preferably less than 10%, preferably less than 5%, preferably less than a 2% change in percent alkane conversion between the first and twentieth iteration, preferably between the first and fifteenth iteration, preferably between the first and tenth iteration, preferably between the first and fifth iteration, preferably between the first and fourth iteration, preferably between the first and third iteration, preferably between the first and second iteration.

In a preferred embodiment, there is a less than a 10% change in percent olefin selectivity relative to a total percentage of products formed between the first and second iteration, preferably less than 5%, preferably less than 4%, preferably less than 3%, preferably less than 2%, preferably less than a 1% change in percent olefin selectivity relative to a total percentage of products formed between the first and second iteration. In another embodiment, there is a less than a 20% change in percent olefin selectivity relative to a total percentage of products formed, preferably less than 15%, preferably less than 10%, preferably less than 5%, preferably less than 2% change in percent olefin selectivity relative to a total percentage of products formed between the first and twentieth iteration, preferably between the first and fifteenth iteration, preferably between the first and tenth iteration, preferably between the first and fifth iteration, preferably between the first and fourth iteration, preferably between the first and third iteration, preferably between the first and second iteration.

The examples below are intended to further illustrate methods protocols for preparing and characterizing the dehydrogenation catalyst of the present disclosure. Further, they are intended to illustrate assessing the properties and performance of these dehydrogenation catalysts. They are not intended to limit the scope of the claims.

Example 1

Catalyst Synthesis

The catalyst samples were prepared by an impregnation method through soaking with excess ethanol as solvent. The support material $\gamma$-$Al_2O_3$ (surface area of 141 m$^2$/g) was received from Inframat Advanced Materials, Manchester, UK, while CaO (surface area of 4 m$^2$/g) was received from Loba Chemie, India. Before metal loading, the $\gamma$-$Al_2O_3$ and CaO supports were calcined under pure $N_2$ flow at 500° C. for 4 hours to remove moisture and volatile compounds. The calcined $\gamma$-$Al_2O_3$ sample was place in a beaker and ethanol was added. A desired amount of vanadyl acetyl acetonate and CaO were then added to the beaker and the mixture was left under stirring for 12 hours. The mixture was then placed under sonication for 10 minutes. The mixture was filtered and dried at room temperature under atmospheric conditions evaporating ethanol. Following the natural evaporation and drying, the sample was placed in an oven at 100° C. for 24 hours in order to slowly remove any remaining solvent. The dried sample was then reduced with hydrogen (10% $H_2$ and 90% Ar) at 500° C. in a specially designed fluidized bed reactor. Finally, the reduced sample was calcined under air at 500° C. for 4 hours to obtain the oxide form of the catalyst. After this treatment, the catalyst displayed a yellow color indicating the presence of $V_2O_5$ on the support surface. In this manner, two catalyst samples were prepared with CaO to $\gamma$-$Al_2O_3$ weight ratios of 1:4 and 1:1, respectively while keeping constant a 10 wt % vanadium loading ($VO_x$/CaO-$\gamma Al_2O_3$ (1:4) and $VO_x$/CaO-$\gamma Al_2O_3$ (1:1)). A third sample was prepared using pure CaO as support and 10 wt % vanadium loading ($VO_x$/CaO). The measured BET surface areas of the prepared catalysts ranged from 14 to 25 m$^2$/g.

Example 2

X-Ray Diffraction (XRD) Analysis and Characterization of the Prepared Catalysts

The crystallographic structure of the catalyst samples and the bare supports were investigated using X-ray diffraction (XRD) analysis. The XRD patterns of all the samples were recorded on a Rigaku Miniflex diffractometer with monochromatic Cu K$\alpha$ radiation of $1.5406 \times 10^{-1}$ nm wavelength, an electrical current of 50 mA, an electrical voltage of 10 kV and a scan rate of 2° per minute (normal scan rate) within the 2θ range from 10°-90° with a 0.02 step size.

Figure 1B:
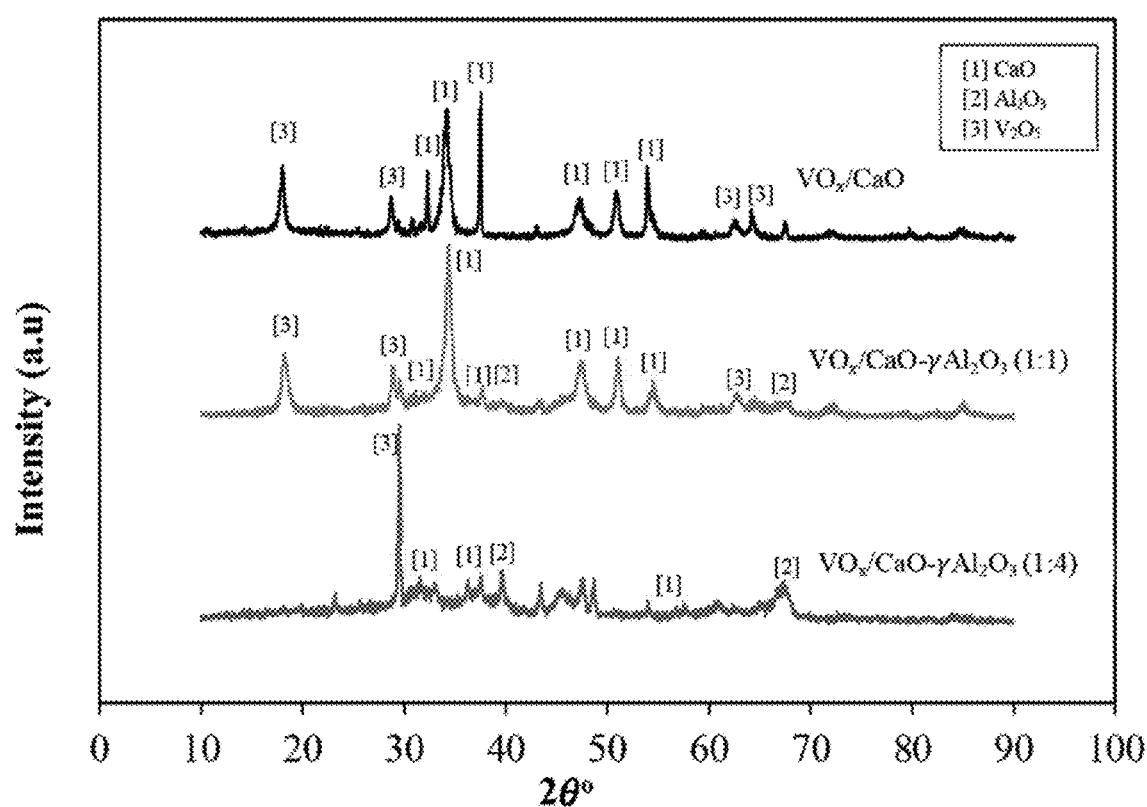
FIG. 1B is the XRD patterns of the three prepared catalyst samples $VO_x/CaO$-γ-$Al_2O_3$ (1:4), $VO_x/CaO$-γ-$Al_2O_3$ (1:1), and $VO_x/CaO$ alone with the peaks attributed to each of their components $V_2O_5$, γ-$Al_2O_3$, and CaO indicated.

FIG. 1A shows the XRD patterns of the three $VO_x$/CaO-$\gamma$-$Al_2O_3$ catalyst samples (different CaO/$\gamma$-$Al_2O_3$ ratios) as well as bare CaO support, bare $\gamma$-$Al_2O_3$ support, and $V_2O_5$ for comparison. The XRD pattern of $V_2O_5$ shows well defined crystal structures at 2θ angles of 12.8°, 17.4°, 19.7°, 24.1°, 28.2°, 43.3°, and 48.2°. The $\gamma$-$Al_2O_3$ samples give two peaks at 2θ angles of 48° and 67°, which are consistent with previous studies. The XRD pattern of CaO shows well defined reflections at 2θ angles of 32°, 38° and 55°, this is also in line with the previously published literature [R. Molinder, T. P. Comyn, N. Hondow, J. E. Parkerc, V. Duponta, In situ X-ray diffraction of CaO based $CO_2$ sorbents, Energy Environ. Sci., 5 (2012) 8958-8969.—incorporated herein by reference in its entirety]. FIG. 1B shows the XRD patterns of the three XRD patterns of the three $VO_x$/CaO-$\gamma$-$Al_2O_3$ catalyst samples with different amounts of CaO and $\gamma$-$Al_2O_3$ and with the same amount of $VO_N$. For the $VO_x$/CaO-$\gamma Al_2O_3$ (1:1) and $VO_x$/CaO-$\gamma Al_2O_3$ (1:4) samples, the $\gamma$-$Al_2O_3$ peaks appeared at 2θ angles of 48° and 67°. The peaks which appeared at 32°, 38°, and 55° can be attributed to CaO. All three samples confirmed these peaks and the intensity of the CaO peaks decreased when the content of CaO in the sample decreased. The 19.5° peak on the $VO_x$/CaO-$\gamma Al_2O_3$ (1:1) and $VO_x$/CaO catalyst samples can be ascribed to $V_2O_5$ crystals. Small $V_2O_5$ peaks were also detected in the CaO sample at 2θ angles above 60°. This observation indicates that the VOx species in the catalyst samples mainly appeared as a highly dispersed amorphous phase on the support samples.

The XRD patterns of the three catalyst samples show few peaks corresponding to the vanadium oxide species. The similar XRD patterns of the $VO_x$/CaO-$\gamma Al_2O_3$ (1:4) and $VO_x$/CaO-$\gamma Al_2O_3$ (1:1) samples further confirmed the non-crystalline appearance of $VO_x$ species. This can be ascribed to the fact that the $VO_x$ species in the catalyst samples has a highly dispersed amorphous phase on the $\gamma$-$Al_2O_3$ and CaO surface. There is also the alternative possibility of the presence of small virtually undetectable by XRD $V_2O_5$ crystalline nanoparticles with a high level of dispersion on the $\gamma$-$Al_2O_3$ and/or CaO support. This observation is consistent with other available findings in previously published literature. The other probable phases, the $AlV_2O_9$ and the $CaV_2O_6$ phase were also not detected in any of the catalyst samples. One can infer from this observation that the reaction between the vanadium and the support materials $\gamma$-$Al_2O_3$ and/or CaO is negligible during the treatment, even at 750° C.

Example 3

Laser Raman Spectroscopy Analysis and Characterization of the Prepared Catalysts The molecular structures of various metal oxide species supported on CaO-$\gamma$-$Al_2O_3$ and CaO were analyzed using a Horiba Raman spectrometer attached to a confocal microscope. For each experiment, 0.5 g of sample was dehydrated under dry air for an hour at 500° C. and then cooled to ambient temperature. Each sample was analyzed using a Raman spectrometer with a thermoelectrically cooled CCD detector (−73° C.). An argon ion laser line of 532 nm wavelength was used to excite the catalyst samples. The Raman spectrometer was used for measuring and recording the spectra produced from the excitation with a resolution of 1 cm$^{-1}$ at room temperature.

Figure 2A:
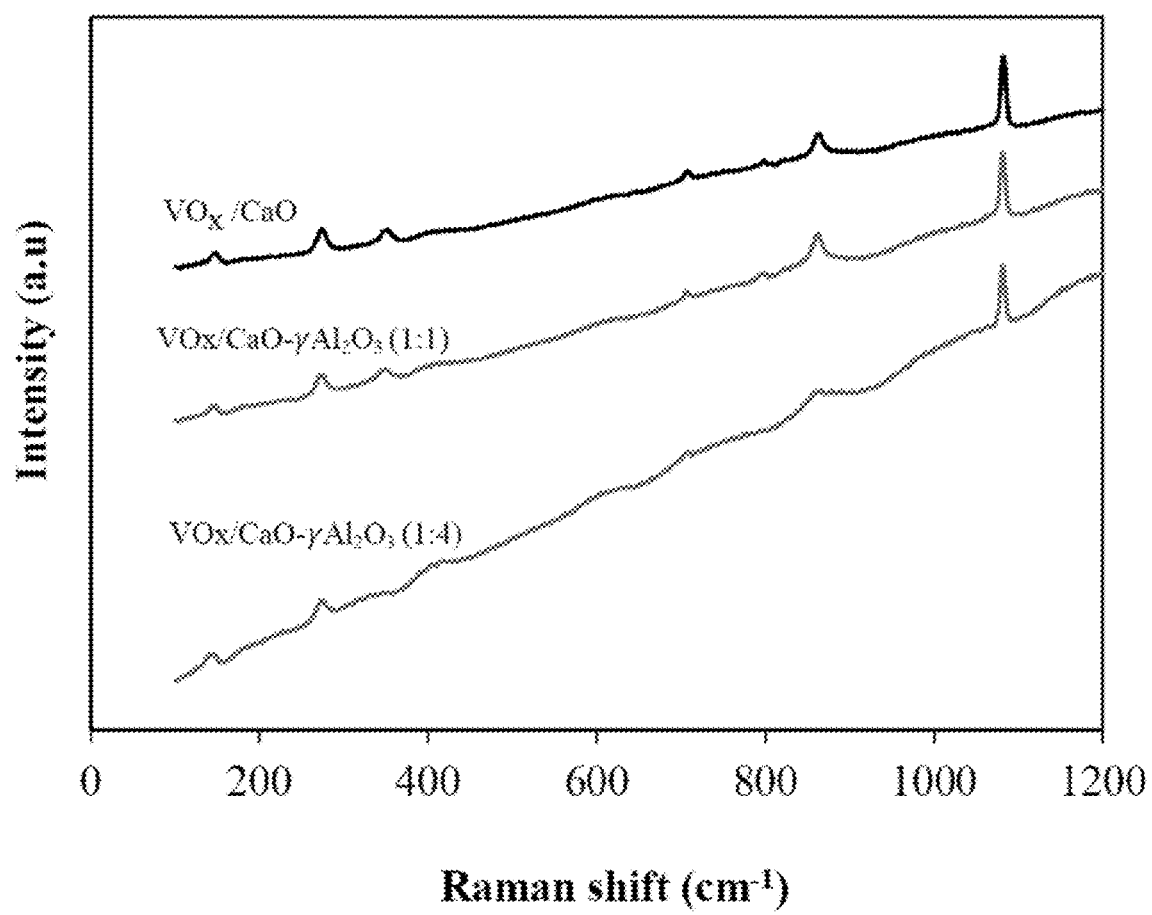
FIG. 2A is the laser Raman spectroscopy spectra of the prepared catalyst samples $VO_x/CaO$-γ-$Al_2O_3$ (1:4), $VO_x/CaO$-γ-$Al_2O_3$ (1:1), and $VO_x/CaO$ alone.
Figure 2B:
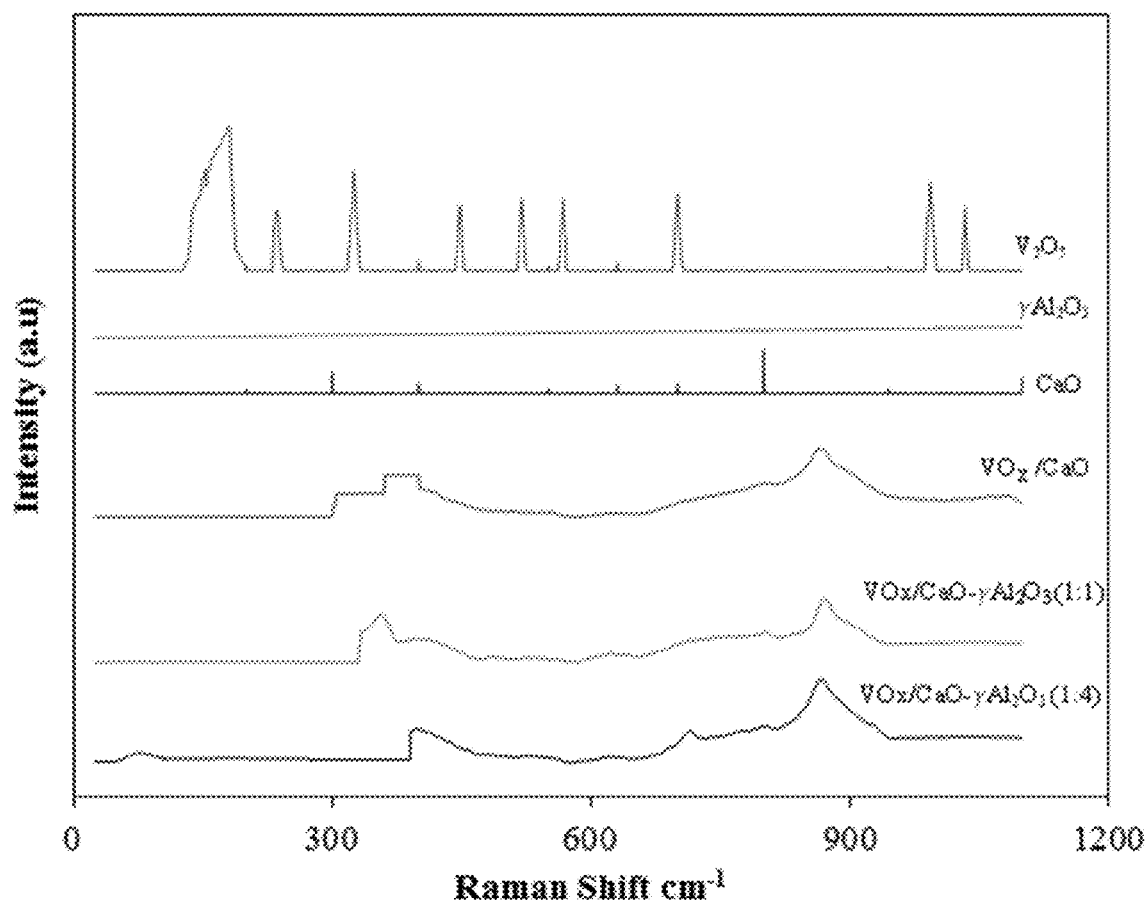
FIG. 2B is the laser Raman spectroscopy spectra of the prepared catalyst samples $VO_x/CaO$-γ-$Al_2O_3$ (1:4), $VO_x/CaO$-γ-$Al_2O_3$ (1:1), and $VO_x/CaO$) as well as their components $V_2O_5$, γ-$Al_2O_3$, and CaO.

FIG. 2A presents the Raman spectra of the samples that were obtained at ambient temperature. FIG. 2B also includes the Raman spectra of bare CaO and γ-$Al_2O_3$ supports and $V_2O_5$ samples. The Raman spectra analysis indicates that all of the three catalyst samples $VO_x$/CaO, $VO_x$/CaO-γ-$Al_2O_3$ (1:1) and $VO_x$/CaO-γ-$Al_2O_3$ (1:4) contain both monovanadate and polyvanadate with minute crystal particles of $V_2O_5$. The broad bands in the range of 670-945 $cm^{-1}$ such as 870 $cm^{-1}$ are attributed to the stretching mode of the polyvanadate species (V—O—V). The 945-1030 $cm^{-1}$ band is ascribed to the stretching mode of V=O. The narrow 1030-1035 $cm^{-1}$ band and broad 1069 $cm^{-1}$ band are ascribed to the stretching mode of the V=O bond in isolated monovanadate surface species. All other bands appearing around 100, 180, 235, 285, 325, 345, 448, 520, 567, and 993 $cm^{-1}$ are ascribed to bulk $V_2O_5$ crystals. In addition, all the catalyst samples have slight peaks at 1030-1035 $cm^{-1}$ which corresponds to monovanadate species.

Example 4

Fourier Transform Infrared (FTIR) Spectroscopy Analysis and Characterization of the Prepared Catalysts A Nicolet 6700 Thermo Fischer Scientific instrument was used to record the Fourier transform infrared (FTIR) spectra of the synthesized catalyst samples and the bare support γ-$Al_2O_3$ and CaO samples. For analysis, 3 mg of sample was uniformly mixed with 0.4 g of potassium bromide. The infrared spectra of pelletized samples were later collected in the range of 400-4000 $cm^{-1}$.

Figure 3A:
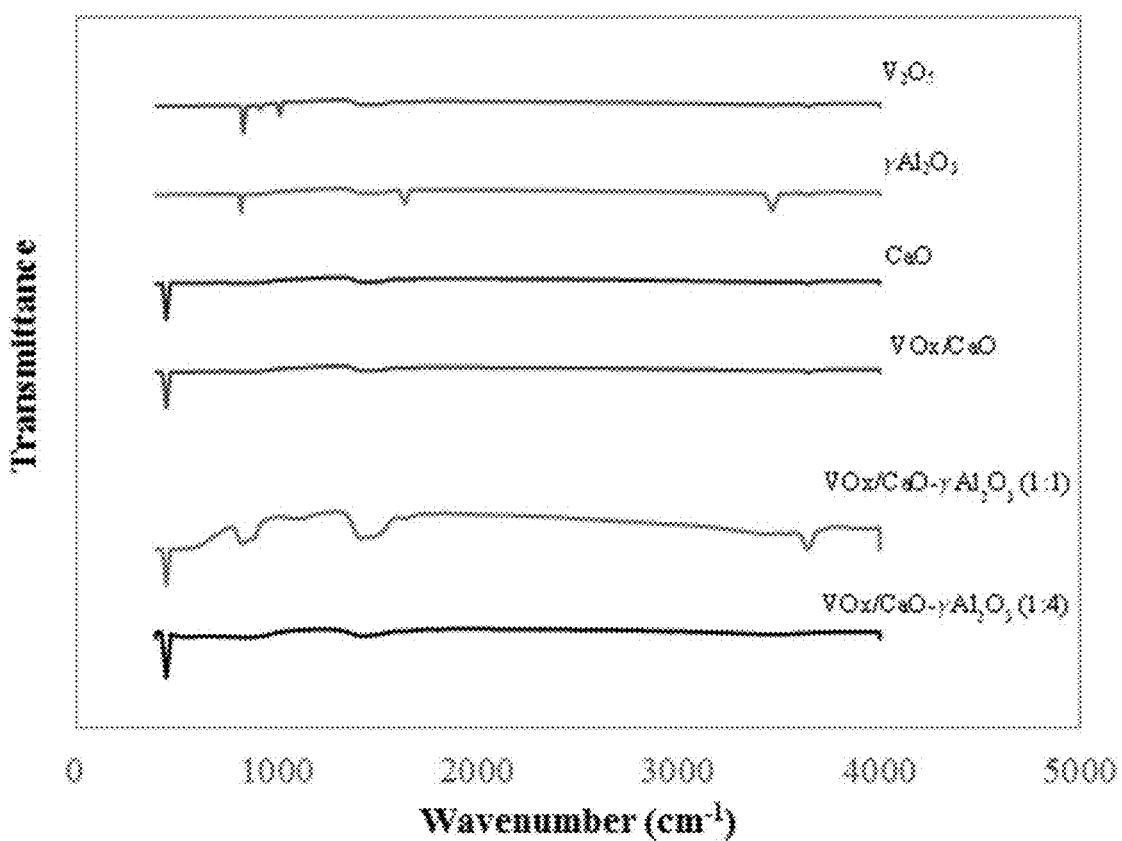
FIG. 3A is the Fourier transform infrared (FTIR) absorption spectra of the prepared catalyst samples $VO_x/CaO$-γ-$Al_2O_3$ (1:4), $VO_x/CaO$-γ-$Al_2O_3$ (1:1), and $VO_x/CaO$ as well as their components $V_2O_5$, γ-$Al_2O_3$, and CaO.

FIG. 3A displays the FTIR spectra of $VO_x$/CaO-γ-$Al_2O_3$ (1:4), $VO_x$/CaO-γ-$Al_2O_3$ (1:1), and $VO_x$/CaO catalysts as well as CaO, γ-$Al_2O_3$, and $V_2O_5$ samples for comparison. The strong infrared bands at 3464 $cm^{-1}$, 1629 $cm^{-1}$, 880 $cm^{-1}$ and 821 $cm^{-1}$ as shown in the FTIR spectra representing γ-$Al_2O_3$ are attributed to the stretching vibration of the Al—O bond [A. Imtiaz, M. A. Farrukh, M. Khaleeq-ur-rahman, R. Adnan, Micelle-Assisted Synthesis of $Al_2O_3$.CaO Nanocatalyst: Optical Properties and Their Applications in Photodegradation of 2,4,6-Trinitrophenol, Scientific World Journal. 2013 (2013) 1-11.—incorporated herein by reference in its entirety]. CaO has strong infrared bands corresponding to 450 $cm^{-1}$, 1410 $cm^{-1}$, and 3650 $cm^{-1}$ as shown in the spectra. These peaks may be attributed to lattice vibrations of CaO [M. Sadeghi, M. H. Husseini, A Novel Method for the Synthesis of CaO Nanoparticle for the Decomposition of Sulfurous Pollutant, J. Appl. Chem. Res. 7 (2013) 39-49.—incorporated herein by reference in its entirety]. Strong infrared bands were observed at 833 $cm^{-1}$, 1014 $cm^{-1}$, and 1629 $cm^{-1}$ on the $V_2O_5$ vanadium oxide curve.

Figure 3B:
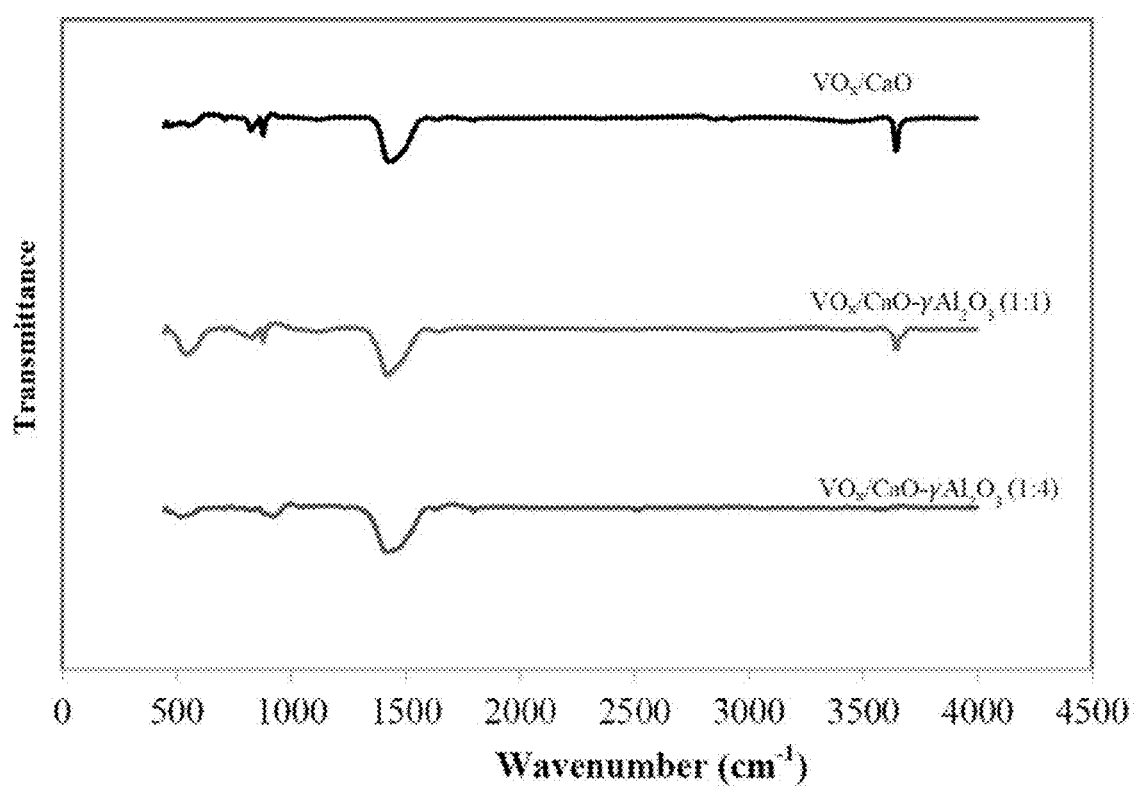
FIG. 3B is the FTIR absorption spectra of the prepared catalyst samples $VO_x/CaO$-γ-$Al_2O_3$ (1:4), $VO_x/CaO$-γ-$Al_2O_3$ (1:1), and $VO_x/CaO$ alone.

FIG. 3B displays the FTIR spectra of $VO_x$/CaO-γ-$Al_2O_3$ (1:4), $VO_x$/CaO-γ-$Al_2O_3$ (1:1), and $VO_x$/CaO catalyst samples alone. The absorption peak at 450 $cm^{-1}$, 1410 $cm^{-1}$, and 3650 $cm^{-1}$ in all three catalyst samples $VO_x$/CaO-γ-$Al_2O_3$ (1:4), $VO_x$/CaO-γ-$Al_2O_3$ (1:1), and $VO_x$/CaO confirms the presence of CaO in the catalysts. The band at 1014 $cm^{-1}$ and 1629 $cm^{-1}$ confirms the presence of $V_2O_5$ in the catalyst samples and the band at 829 $cm^{-1}$ and 880 $cm^{-1}$ confirms the presence of γ-$Al_2O_3$ in the $VO_x$/CaO-γ-$Al_2O_3$ (1:4) and $VO_x$/CaO-γ-$Al_2O_3$ (1:1) catalyst samples. The peak at 1014 $cm^{-1}$ corresponds to the strong terminal oxygen bond ($V^{5+}$=O) [X. Zhou, G. Wu, J. Wu, H. Yang, J. Wang and G. Gao, Carbon black anchored vanadium oxide nanobelts and their post-sintering counterpart ($V_2O_5$ nanobelts) as high performance cathode materials for lithium ion batteries, Phys. Chem. Chem. Phys, 16 (2014) 3973-3982.—incorporated herein by reference in its entirety].

Example 5

Scanning Electron Microscopy (SEM) and Energy Dispersive X-Ray Spectroscopy (EDXS) Analysis and Characterization of the Prepared Catalysts The elemental analyses of the prepared samples were conducted using energy dispersive X-ray spectroscopy (EDXS). For analysis, the catalyst samples were dispersed on a stub that is tapped with copper. Each of the samples were coated with gold in order to eliminate charge build up, obtain better contrast, and enhance visibility at magnification of up to one million times. The sample was analyzed by scanning electron microscopy (SEM), while ensuring that the microscope is aligned in order to avoid a lack of sharpness and focus. An electron beam is incident across the catalyst sample resulting in the generation of secondary and back scattered electrons, which are used to form images and X-rays which were used to obtain elemental constitutions of the catalyst samples.

Figure 4:
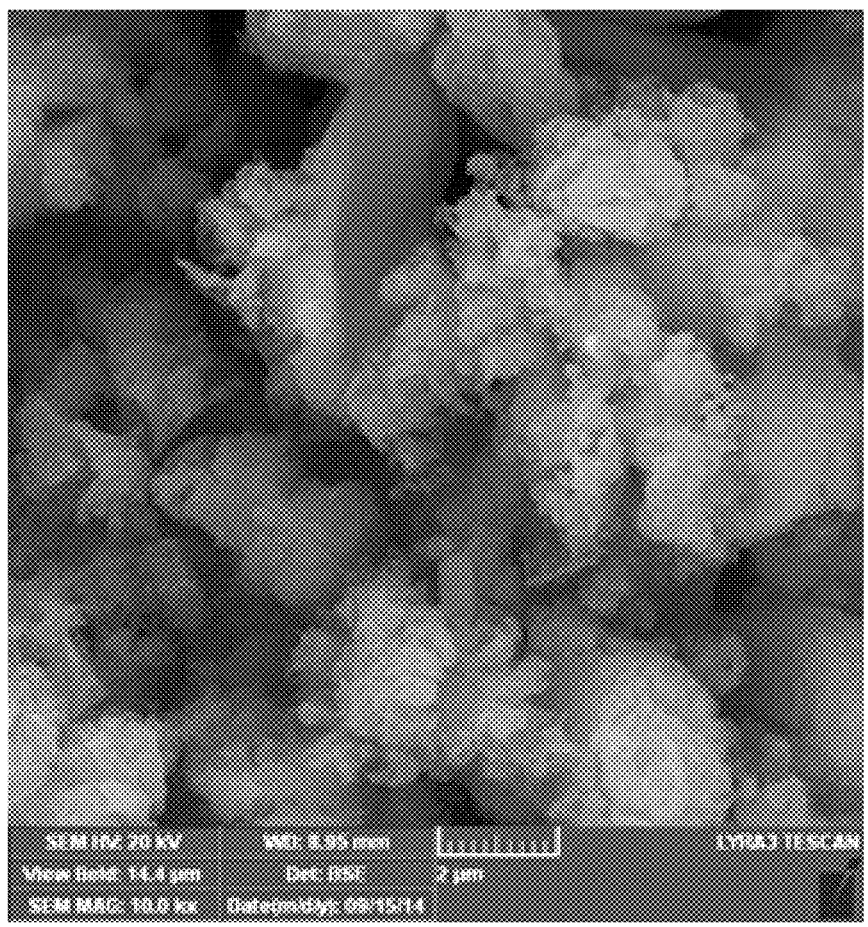
FIG. 4 is a scanning electron microscopy (SEM) image of the prepared $VO_x/CaO$-γ-$Al_2O_3$ (1:1) catalyst sample.
Figure 5:
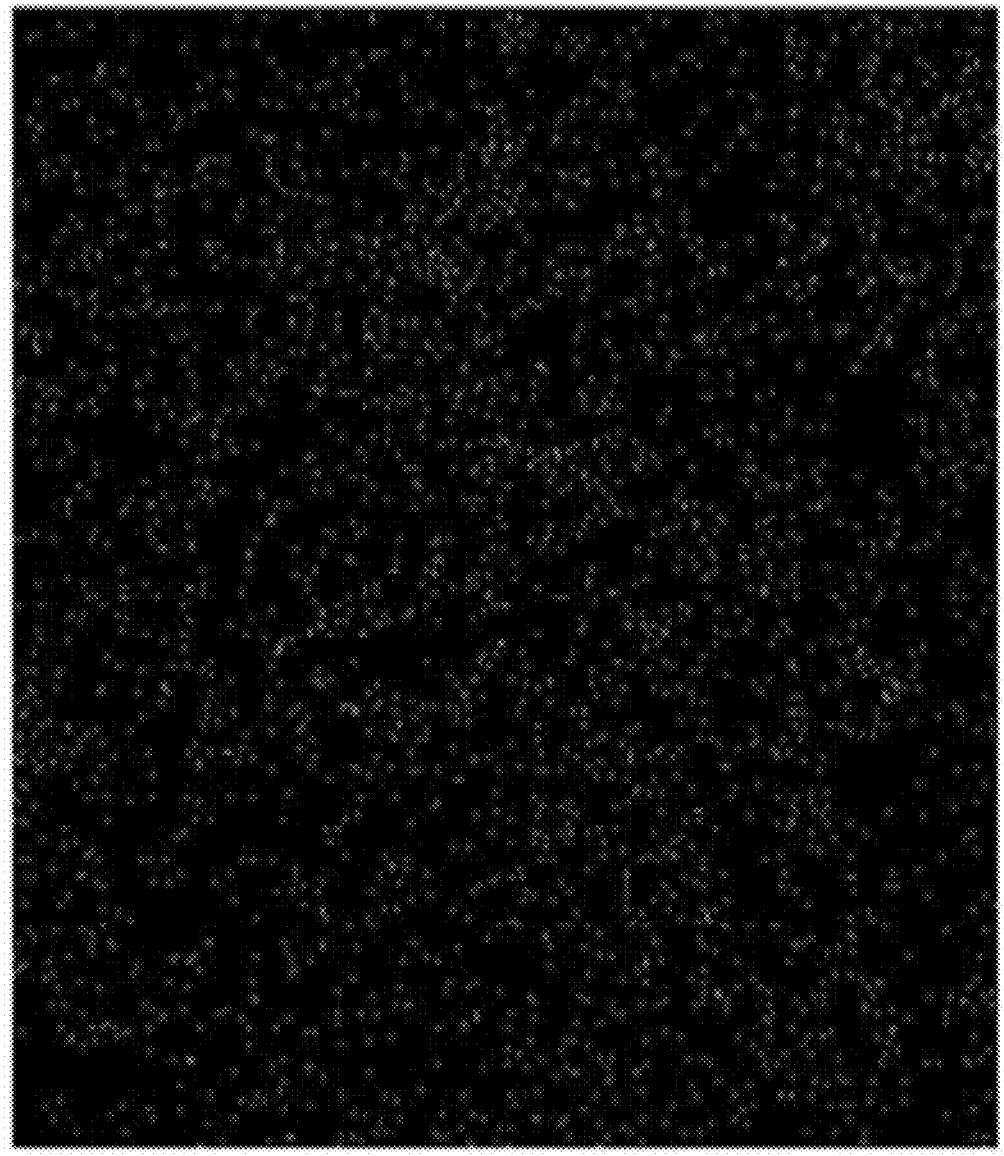
FIG. 5 is a scanning electron microscopy energy dispersive X-ray analysis (SEM-EDX) image showing elemental mapping of vanadium the prepared $VO_x/CaO$-γ-$Al_2O_3$ (1:1) catalyst sample.

The SEM together with the EDXS analysis was carried out to determine the metal dispersion. FIG. 4 presents a representative field emission scanning electron microscope image of one of the catalyst samples, $VO_x$/CaO-γ-$Al_2O_3$ (1:1). The images of the elemental distribution can be used to envisage the quality of the dispersion. FIG. 5 shows the dispersion of the vanadium element over the oxygen carrier samples in the $VO_x$/CaO-γ-$Al_2O_3$ (1:1) catalyst. It is evident that the vanadium particles are well dispersed on the CaO-γ$Al_2O_3$ support. This indicates superior dispersion of the $VO_x$ over the CaO-γ$Al_2O_3$ support.

Example 6

Temperature Programmed Reduction-Oxidation (TPR/TPO) Characterization of the Prepared Catalysts' Reducibility and Oxygen Carrying Capacity The reduction temperature and reducibility of the catalyst samples were determined using the temperature programmed reduction (TPR) technique. A Micrometrics Auto-Chem II 2920 analyzer was used to conduct $H_2$-TPR experiments at 101.3 KPa. For TPR analysis, 0.05 g of catalyst sample was loaded in a U-shaped quartz tube using glass wool to hold the catalyst particles inside. The tube was inserted into retaining nuts and O-rings and then positioned in tube ports placed in a heater. Before analysis the sample was pretreated under an argon (Ar) flow at 500° C. to remove any volatile components. After pretreatment, the sample was completely oxidized by circulating a gas mixture of 5% $O_2$ and helium (He) balance, at 500° C. with a heating rate of 10° C./min. The sample was then cooled down to ambient temperature under argon flow to ensure flushing out of any gas phase $O_2$ that may have been trapped in the catalyst bed. The temperature programmed reduction experiment was carried out by circulating a gas stream of 10% $H_2$/Ar at 50 $cm^3$/min. At these conditions, the sample temperature was raised from room temperature to 850° C. at a heating rate of 10° C./min. With the increasing bed temperature, hydrogen begins to react with the solid phase metal oxides producing water vapor. This water vapor was trapped by circulating the exit stream through a clod trap containing molecular sieves. The water free outlet gas stream was passed through a calibrated thermal conductivity detector (TCD) which detects the variation of the hydrogen concentration due to the reduction of the catalyst samples.

TPR/TPO is an important technique for the characterization of gas phase oxygen free ODH catalysts given that is simulates reduction/oxidation of the catalysts during the actual ODH reaction with propane. It gives information about the reducibility and regeneration ability of the catalyst. Formula (VII) gives the equation of the TPR reaction and formula (VIII) gives the equation of the ODH of propane reaction.

$$V_2O_5 + 2H_2 \rightarrow V_2O_3 + 2H_2O \tag{VII}$$

$$C_3H_8 + \frac{1}{2}V_2O_5 \rightarrow C_3H_6 + H_2O + \frac{1}{2}V_2O_3 \tag{VIII}$$

In can be seen that in both the TPR reaction (formula (VII)) and the ODH or propane reaction (formula (VIII)) $V_2O_5$ is reduced to $V_2O_3$. In contrast, the TPO cycle represents the catalyst regeneration cycle following the reduction in the TPR reaction. Formula (IX) gives the equation of the TPO reaction.

$$V_2O_3 + O_2 \rightarrow V_2O_5 \tag{IX}$$

In addition, the TPR/TPO data can be further processed to determine the oxygen carrying capacity of the catalysts for the oxidative dehydrogenation of propane without any additional gas phase oxygen (catalyst reduction cycle). Therefore, TPR analysis indicates the temperature range of catalyst activation and the amount of available lattice oxygen for the ODH of propane.

Figure 6:
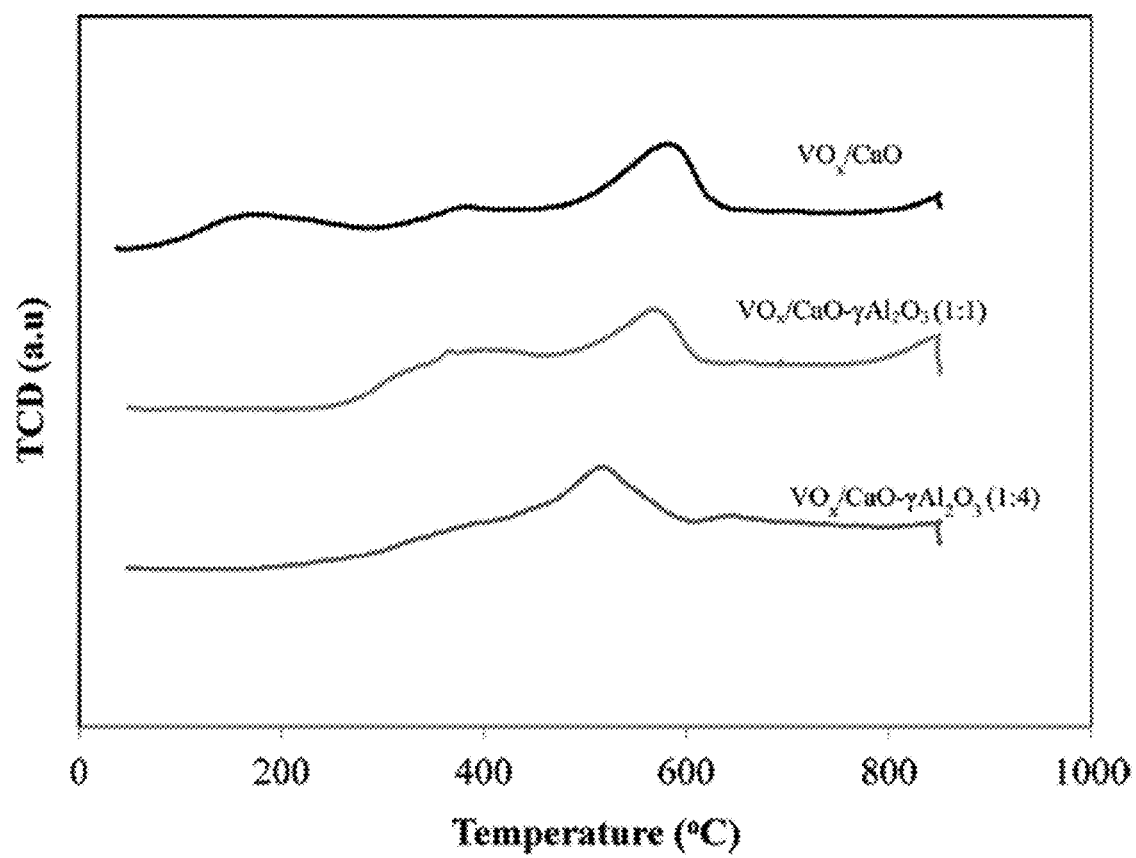
FIG. 6 is the temperature programmed reduction (TPR) profiles of the prepared $VO_x/CaO$-γ-$Al_2O_3$ (1:4), $VO_x/CaO$-γ-$Al_2O_3$ (1:1), and $VO_x/CaO$) catalyst samples.

FIG. 6 presents the TPR profiles of the $VO_x/CaO$-$\gamma$-$Al_2O_3$ catalysts with different CaO to $\gamma$-$Al_2O_3$ ratios. It can be seen that all three catalyst samples have similar reduction profiles and generally undergo most reduction between 350 and 620° C. The TPR profiles show that the $VO_x/CaO$ catalyst sample has two humps between 95-287° C. and 300-430° C. while $VO_x/CaO$-$\gamma$-$Al_2O_3$ (1:1) shows only one hump between 260 and 450° C. due to the highly reducible $VO_x$ species that appeared on the support surfaces. The low temperature reduction hump with the $VO_x/CaO$-$\gamma$-$Al_2O_3$ (1:4) sample was less pronounced than the other two samples. In addition to the initial reduction humps, all three catalyst samples exhibit a major reduction peak between 520-580° C. While the initial reduction hump can be attributed to the reduction of bulk $V_2O_5$ like surface species, the single major peak attributed to each catalyst sample confirmed the presence of monomeric and polymeric $VO_x$ species at the surface and the relative absence of crystalline $V_2O_5$ nanoparticles, which gives the indication of high reducibility. For all the catalyst samples, there was no peak attributed to CaO or $Al_2O_3$. This is due to the fact that calcium and aluminum are higher in the electrochemical series as compared to vanadium and hydrogen. Indeed, the temperatures that will be required for the reduction of CaO and $Al_2O_3$ with hydrogen are higher than the temperature range considered in the TPR experiment. However, the reduction peak temperatures of the samples significantly varied with the variation of the CaO content in the catalyst formulation. The peak temperature of the lowest CaO containing $VO_x/CaO$-$\gamma$-$Al_2O_3$ (1:4) sample was 515° C. With increasing CaO content, the $VO_x/CaO$-$\gamma$-$Al_2O_3$ (1:1) sample, the peak temperature shifted to 560° C. The CaO supported $VO_x/CaO$ sample shows the highest peak temperature at 583° C. Previously, Bosc, et al. and Koranne, et al. reported similar reduction behavior for CaO containing vanadium catalysts [H. Bosc, J. K. Bert, J. G. Van Ommen, P. J. Gellings, Factors influencing the temperature programmed reduction profiles of vanadium pentoxide, J. Chem. Soc. Faraday Trans 80 (1984) 2479-2488; and M. M, Koranne, J. G. Goodwin, G. Marcelin, Characterization of silica and alumina supported vanadia catalysts using temperature programmed reduction, J. Catal. 148 (1994) 369-377.—each incorporated herein by reference in its entirety]. The shift of reduction temperature is possibly due to the increased active site metal-support interaction introduced by the addition of CaO The TPR data was further processed to evaluate the degree of reduction for the three catalyst samples. The degree of reduction can be defined as the percentage of $VO_x$ reduced to the actual quantity of vanadium oxide available in the catalyst. The exposed reducible $VO_x$ was calculated from the amount of hydrogen uptake evaluated using numerical integration of the resulting temperature programmed reduction peak area. The mass of reducible vanadium oxide in the catalyst sample was evaluated using molar volume of gas at standard temperature/pressure (STP), volume of hydrogen uptake, molecular weight of vanadium oxide and stoichiometric number of hydrogen in the gas-solid reaction involved in reduction. The percentage of vanadium oxide reduction can be calculated using the relation of formula (X) and formula (XI).

$$\% \text{ reduced} = \frac{W_V}{W_0} \times 100 \tag{X}$$

$$W_V = \frac{MW_V \times V_{H_2}}{v \times V_g} \tag{XI}$$

In this formula, $W_V$ is the amount of reduced vanadium (g), $MW_v$ is the molecular weight of vanadium (g/mol), $V_{H2}$ is the volume of reacted hydrogen ($cm^3$ at STP), $V_g$ is the molar volume of gas ($cm^3$/mol at STP), $W_0$ is the initial weight of vanadium (g) and $v$ is the stoichiometric number of hydrogen based on the reaction stoichiometry presented in formula (I). Assuming that $V_2O_5$ is the initial reducible catalyst species on the support, then the reduction reaction equation of formula (VII) applies.

$$V_2O_5 + 2H_2 \rightarrow V_2O_3 + 2H_2O \tag{VII}$$

Table 1 shows the hydrogen uptake and the percentage reduction of the catalyst samples. It can be seen from this table that the hydrogen uptake was increased with increasing the CaO content in the catalyst samples. The higher hydrogen uptake is possibly due to the higher dispersion of vanadium species as observed in the low temperature reduction humps of the $VO_x/CaO$-$\gamma$-$Al_2O_3$ (1:1) and $VO_x/CaO$ catalysts. The increased basicity with higher quantities of CaO also contributes to the increased hydrogen consumption, given the acidic nature of hydrogen gas, which has higher affinity to catalysts with higher basicity. The hydrogen gas in solution is acidic and will have higher reactivity with the catalyst of high basicity.

TABLE 1

Temperature programmed reduction (TPR) data comparing hydrogen consumption for the three prepared catalyst samples of varying CaO content

| Sample | H$_2$ uptake (mmol/g) (% reduction) | | | | Average | % Error | Uptake of H$_2$ (cm$^3$ STP) | % reduction |
|---|---|---|---|---|---|---|---|---|
| | 1$^{st}$ | 2$^{nd}$ | 3$^{rd}$ | 4$^{th}$ | | | | |
| VO$_x$/CaO-γ-Al$_2$O$_3$ (1:4) | 1.9 (48%) | 1.8 (46%) | 1.8 (45%) | 1.8 (45%) | 1.8 | 1.6 | 2.12 | 48.21 |
| VO$_x$/CaO-γ-Al$_2$O$_3$ (1:1) | 2.6 (65%) | 2.5 (63%) | 2.4 (62%) | 2.4 (62%) | 2.5 | 2.5 | 2.87 | 65.27 |
| VO$_x$/CaO | 2.9 (72%) | 2.8 (70%) | 2.8 (70%) | 2.7 (69%) | 2.8 | 1.8 | 3.18 | 72.32 |

In order to assess the oxygen carrying capacity and stability under redox cycles, the catalyst samples were subjected to repeated consecutive reduction and re-oxidation TPR and TPO cycles. The hydrogen consumption in each TPR cycle was measured using the calibrated TCD signals. The percentage of reduction of the catalyst in each TPR cycle calculated from the hydrogen uptake data is presented in Table 1. It is apparent that in the repeated TPR/TPO cycles, the hydrogen uptake for the catalyst samples was within a 2.5% error range (Table 1). For all three catalyst samples, the hydrogen uptake remains consistent over the repeated TPR/TPO cycles although the percentage reduction of each sample varies as discussed above. This observation indicates that the oxygen carrying capacity of the catalyst remains stable over the repeated redox (TPR/TPO) cycles. Additionally, the stable value of the hydrogen consumption indicates good stability of the present catalysts.

Example 7

NH$_3$-Temperature Programmed Desorption (NH$_3$-TPD) Characterization of the Prepared Catalysts' Acidity The acidity and acid strength of the catalysts were investigated using ammonia in a temperature programmed desorption (TPD) analysis. The NH$_3$-TPD desorption kinetic analysis also helps evaluating the metal-support interactions of the supported catalysts. In the context of the present disclosure, the NH$_3$-TPD experiments were conducted using an AutoChem II 2029 Analyzer received from Micromeritics, USA. Similar to the TPR experiments, 0.05 g (or 0.5 g) of catalyst was first loaded into the U-shaped quartz container and degassed for 2 hours at 500° C. under argon (Ar) flow at 30 mL/min. The sample was then cooled to 120° C. and brought to saturation with ammonia using a NH$_3$/He gas mixture (5% NH$_3$/He) at a rate of 50 mL/min. Following the ammonia saturation, the system was purged with helium at a temperature of 100° C. at a rate of 50 cm$^3$/min in order to remove any gas phase ammonia in the system and unabsorbed ammonia trapped in the catalyst bed. For desorption analysis, the catalyst bed temperature was raised from room temperature to 750° C. at 10° C./min. The ammonia chemisorbed was desorbed as the temperature elevated to 750° C. The ammonia concentration of the effluent gas was monitored by the thermal conductivity detector.

The acid sites of the three catalyst samples were characterized by TPD using NH$_3$ as the basic probe molecule. The area of the TPD curve peak gives acid amount while the position of the peak indicates the acid distribution in the catalyst samples. Ammonia TPD can distinguish sites only by sorption strength; hence its shortcoming lies in its inability to differentiate between Lewis and Bronsted acid sites.

Figure 7:
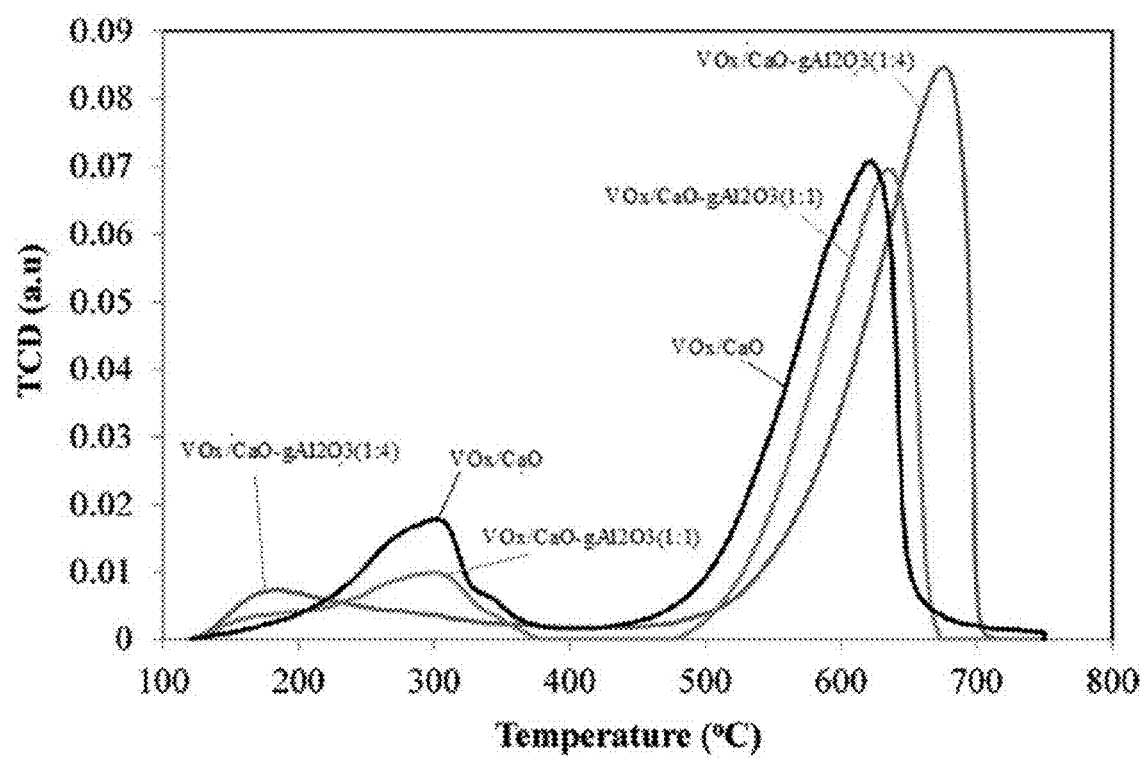
FIG. 7 is the ammonia temperature programmed desorption ($NH_3$-TPD) profiles of the prepared $VO_x/CaO$-γ-$Al_2O_3$ (1:4), $VO_x/CaO$-γ-$Al_2O_3$ (1:1), and $VO_x/CaO$) catalyst samples.

Ammonia was used in this disclosure to make comparisons of the total acidity and acid strength for catalyst samples with different CaO/Al$_2$O$_3$ ratios. FIG. 7 shows the relationship between the desorption volume as a function of the temperature. It can be seen that all three samples show similar TPD profiles although the peak intensity and desorption peaks are shifted with the variation of the CaO/Al$_2$O$_3$ ratios. The NH$_3$-TPD profile for VO$_x$/CaO-γ-Al$_2$O$_3$ (1:4), VO$_x$/CaO-γ-Al$_2$O$_3$ (1:1), and VO$_x$/CaO catalyst samples showed an initial desorption peak at 183° C., 300° C., and 302° C. respectively followed by a high temperature desorption peak at 676° C., 636° C., and 620° C. respectively. The intensity of the high temperature desorption peaks were significantly higher than that of the low temperature peaks. This indicates that the percentage of strong acid sites is much higher than the percentage of weak acid sites. The total acidity of each catalyst sample was calculated by integrating the calibrated TPD profiles. Table 2 shows the uptake of NH$_3$ by the three catalyst samples and their respective temperatures of desorption. The total acidity of the catalyst samples was decreased with the increasing of the CaO content due to the basic nature of the CaO.

TABLE 2

Catalyst acidity of the prepared catalyst samples of varying CaO content as measured by NH$_3$-temperature programmed desorption (NH$_3$-TPD)

| Sample | Peak Temperatures (° C.) | | NH$_3$ Uptake (mmol/g) | | Total |
|---|---|---|---|---|---|
| | Low Temp. | High Temp. | Low Temp. 0.05 g 0.50 g | High Temp. 0.05 g 0.50 g | |
| VO$_x$/CaO-γ-Al$_2$O$_3$ (1:4) | 183 | 676 | 0.0133 0.55 (17%) | 0.0666 2.69 (83%) | 0.0799 3.24 |
| VO$_x$/CaO-γ-Al$_2$O$_3$ (1:1) | 300 | 636 | 0.0163 0.54 (21%) | 0.0612 2.04 (79%) | 0.0775 2.58 |
| VO$_x$/CaO | 302 | 620 | 0.0190 0.55 (26%) | 0.0539 1.58 (74%) | 0.0729 2.13 |

Example 8

NH$_3$-Temperature Programmed Desorption (NH$_3$-TPD) Kinetics Analysis of the Prepared Catalysts Ammonia desorption kinetics were evaluated to determine the active site metal-support interaction of the catalyst samples. The activation energy of ammonia desorption and the pre-exponential factors were estimated by modeling the NH$_3$-TPD experimental data of each catalyst sample. Cvetanovic and Amenonmiya described the desorption rate as a function of temperature which is based upon the following assumptions: i) temperature (T) of desorption has a linear relationship with time (t), ii) the rate of desorption is of first order in coverage, iii) the concentration of ammonia gas through the catalyst bed is uniform, iv) desorbed ammonia has zero feasibility for re-adsorption, and v) the catalyst's surface is homogeneous for the NH$_3$ adsorption, which means the desorption constant (k$_d$=k$_{d0}$ exp(-E/RT) is independent of the surface coverage. Suitable experimental conditions were selected in order to satisfy the assumptions in i) and iii). A high flow of ammonia gas through the catalyst bed was maintained in order to satisfy the assumption in iv). Unimolecular desorption of ammonia was assumed in order to consider the assumption in ii). The ammonia desorption rate at a uniform first order energy of desorption can be evaluated using a component balance of desorbing NH$_3$ in accordance with formula (XII).

$$r_d = -V_m \frac{d\theta}{dt} = k_{do}\theta \exp\left[-\frac{E}{R}\left(\frac{1}{T} - \frac{1}{T_m}\right)\right] \quad \text{(XII)}$$

In this formula, $T_m$ is the centering temperature in °C., $V_m$ is the volume of NH$_3$ adsorbed at saturated conditions in mL/g, $V_d$ is the volume of ammonia desorbed at different temperatures in mL/g, $\theta$ is the surface coverage of the adsorbed species, E is the energy of ammonia desorption in kJ/mol, and k$_{do}$ is the pre-exponential factor in mL g$^{-1}$ min$^{-1}$. Temperature (T) in a TPD experiment has a linear relationship with time (t) given by formula (XIII), formula (XIV), formula (XV), formula (XVI), formula (XVII), and formula (XVIII) wherein T is the desorption temperature at time (t).

$$T = T_0 + \alpha t \quad \text{(XIII)}$$

$$\frac{dT}{dt} = \alpha \quad \text{(XIV)}$$

$$\frac{d\theta}{dt} = \frac{d\theta}{dT}\frac{dT}{dt} = \alpha\frac{d\theta}{dT} \quad \text{(XV)}$$

$$\frac{d\theta}{dT} = -\frac{k_{do}}{\alpha V_m}\theta\exp\left[-\frac{E}{R}\left(\frac{1}{T} - \frac{1}{T_m}\right)\right] \quad \text{(XVI)}$$

$$\theta = 1 - \frac{V_d}{V_m} \quad \text{(XVII)}$$

$$\frac{dV_d}{dT} = \frac{k_{do}}{\alpha}\left(1 - \frac{V_d}{V_m}\right)\exp\left[-\frac{E}{R}\left(\frac{1}{T} - \frac{1}{T_m}\right)\right] \quad \text{(XVIII)}$$

The first order ordinary differential equation was solved using the separation of variable method to obtain formula (XIX).

$$V_d = V_m\left(1 - \exp\left[\ln\left(1 - \frac{V_o}{V_m}\right) - \frac{k_d RT^2}{E\alpha V_m}\left\{\exp\frac{-E}{R}\left(\frac{1}{T} - \frac{1}{T_m}\right) - \exp\frac{-E}{R}\left(\frac{1}{T_0} - \frac{1}{T_m}\right)\right\}\right]\right) \quad \text{(XIX)}$$

In this formula, $V_0$ and $T_0$ are initial volume desorbed in mL/g and the initial desorption temperature. In this formula, R is the universal gas constant in kJ mol$^{-1}$ K$^{-1}$ and the heating rate ($\alpha$) was taken as 10° C./min.

Figure 8:
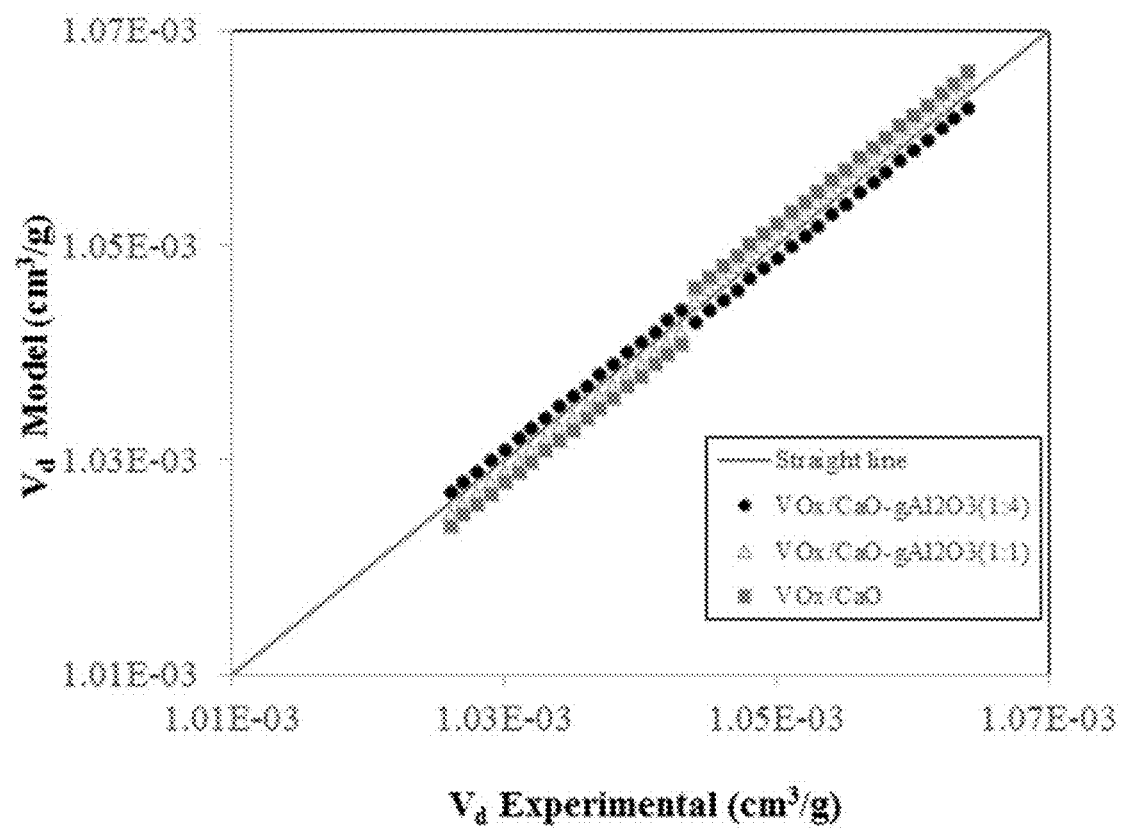
FIG. 8 is a comparison of the experimental data and fitted model of ammonia desorption during $NH_3$-TPD kinetics analysis for the different prepared $VO_x/CaO$-γ-$Al_2O_3$ (1:4), $VO_x/CaO$-γ-$Al_2O_3$ (1:1), and $VO_x/CaO$) catalyst samples.

FIG. 8 shows that the obtained experimental TPD data and the proposed model have good agreement for all catalyst samples. This proves the validity of the proposed desorption model. The TPD data was fitted in the resulting equation (formula (XIII)) using a non-linear regression analysis tool of MATLAB. Hence, the desorption energies and the pre-exponential factors of each catalyst sample were obtained. The norm of the residuals and the coefficient of correlation were calculated for each catalyst sample using MATLAB and MINITAB software at a 95% confidence limit. Table 3 reports the energy of desorption for the three synthesized catalysts. Statistical properties such as the correlation coefficient R$^2$, norm of residuals and 95% confidence intervals were considered in the analysis. The values of R$^2$ and residual norms for all three catalyst samples are close to 1 and 0, respectively, which indicates that the proposed desorption model is applicable.

TABLE 3

Estimated parameter of ammonia-TPD kinetics of the prepared catalyst samples of varying CaO content at 10° C./min

| Sample | E (kJ/mol) | K$_{do}$ (mL/g/min) × 10$^5$ | Norm of residuals × 10$^4$ | V$_{NH3}$ (mmol/g) | V$_{NH3}$ (mL/g) |
|---|---|---|---|---|---|
| VO$_x$/CaO-γ-Al$_2$O$_3$ (1:4) | 39.2 | 3.8 | 2.1 | 3.24 | 72.6 |
| VO$_x$/CaO-γ-Al$_2$O$_3$ (1:1) | 74.8 | 1.3 | 6.4 | 2.58 | 57.7 |
| VO$_x$/CaO | 96.3 | 0.5 | 22.7 | 2.13 | 47.6 |

The values in table 3 show that as the loading of CaO is increased and that of γ-Al$_2$O$_3$ is decreased, the energy of desorption increases. This can be explained based on the amount of ammonia uptake for each of the catalyst samples. The catalyst with the highest desorbed ammonia has the lowest desorption energy while the one with the lowest desorbed ammonia has the highest desorption energy. A similar observation was described by Ghamdi, et al. on γ-Al$_2$O$_3$ supported VO$_x$ catalysts where a higher desorption energy corresponds to a lower amount of NH$_3$ adsorbed from the catalysts. The increase in the activation energy can also be linked to the heterogeneity of the catalyst samples. The interaction between the mixed support and the active site (VO$_x$) also plays a significant role in the value of energy required for ammonia desorption and during the gas-solid reactions involved during the oxidative dehydrogenation of propane under the gas phase oxygen free conditions. Weak active site metal-support interactions will enable high dispersion of the active site which will in turn lead to an increased availability of the lattice oxygen for the oxidative dehydrogenation (ODH) reaction and an easy reaction between $VO_x$ and propane/propylene as opposed to strong active site metal-support interactions. Hence a weaker active site-support interaction will require a lower energy of desorption which means the $VO_x/CaO$-γ-$Al_2O_3$ (1:4) catalyst has the weakest active site-support interaction. However, the moderate active site metal-support interactions as shown by the $VO_x/CaO$-γ-$Al_2O_3$ (1:1) catalyst can be favorable to achieve higher propylene selectivity.

Example 9

Evaluation of the Prepared Catalysts in the Fluidized Oxidative Dehydrogenation (ODH) of Propane The gas phase oxygen free oxidative dehydrogenation (ODH) experiments were conducted in a fluidized CREC Riser Simulator (CREC: Chemical Reactor Engineering Centre). The CREC Riser Simulator, a bench scale fluidized reactor (53 cm³) is very useful for catalyst evaluation and kinetic studies. It has several advantages including simulating fluidized conditions of a riser/downer reactor even with a small amount of catalyst, minimal mass transfer limitations by using small sized catalyst particles, constant residence time distributions, and controlled isothermal conditions. The CREC Riser Simulator reactor operates alongside different accessories which include temperature controllers, a gas chromatograph (GC), a vacuum box, a main power switch, a water pressure indicator and a push button selector. Greater details of the CREC Riser Simulator can be found in Al-Ghamdi, et al.—2012.

Propane ODH runs were carried out at different temperatures ranging from 550° C. to 640° C. while reaction contact times were varied between 10-31 seconds. The reaction temperatures were selected within the reduction temperature range of the catalysts as determined by the TPR analysis, given that the solid catalyst are the only source of oxygen. The ODH of propane experiments were conducted using 0.5 g of catalyst. The oxidized catalyst sample was loaded into the catalyst basket located in the lower shell of the main reactor body of the CREC Riser Simulator. Following the catalyst loading, the system was pressurized up to 30 psi at room temperature to perform a leak test. A stable pressure reading under closed conditions confirmed the absence of any leak. The reactor is then ready to be heated to the desired temperature. During the heating period, the system was maintained under argon (Ar) flow to keep the reactor from any air interference. Once the reactor reached the desired temperature level, the argon flow was stopped. Consequently, the reactor pressure started to decrease sharply. The four port valve of the CREC Riser Simulator was closed, as the reactor pressure approached one atm (14.7 psi). Following the isolation of the reactor, the vacuum pump was turned on to evacuate the vacuum box down to 20.7 kPa (3.75 psi). A preloaded syringe was used to inject 1.2 mL of feed (propane) into the reactor after setting the impeller in motion. The pressure transducer was used to record the pressure profile of the reactor. At the end of the reaction period, the reactor contents were evacuated into the vacuum box. The analysis of the gas product contained in the vacuum box was carried out with the aid of an online GC equipped with three different packed columns. Two of these columns are the carbon-1000 and carbon-1004 columns which are used for separating the hydrogen, oxygen, nitrogen, argon, carbon (IV) oxide, and carbon (II) oxide gases and which are serially connected with the thermal conductivity detector (TCD). A flame ionization detector (FID) was utilized in detecting the hydrocarbons such as propane, propylene, ethane, ethylene, and methane after they were separated with a Haye SepD column. The evaluation of catalyst performance was based on propane conversion, selectivity and yield. Formula (V) gives the definition used in calculating propane conversion. Formula (VI) gives the definition used in calculating selectivity to a product.

$$X_{C_3H_8}(\%) = \frac{\sum_j z_j n_j}{3n_{propane} + \sum_j z_j n_j} \times 100 \tag{V}$$

$$S_j(\%) = \frac{z_j n_j}{\sum_j z_j n_j} \times 100 \tag{VI}$$

In these formulas, $z_j$ and $n_j$ are the number of atoms of carbon and number of moles of gaseous carbon containing product j respectively. In addition, $n_{propane}$ is the number of moles of unconverted propane in the product stream.

The gas phase oxygen free oxidative dehydrogenation (ODH) of propane experiments were conducted in a fluidized CREC Riser Simulator using pure propane (99.95% purity) as feed. Before performing the actual catalytic ODH runs, thermal experiments (without any catalyst) were conducted to confirm the contribution of any thermal conversion. The highest reaction temperature (640° C.) was selected for the thermal experiments. The GC analysis of the thermal runs' products showed mainly unconverted propane and a trace amount of ethane and methane most likely due to thermal cracking of propane in the absence of catalyst.

Figure 9:
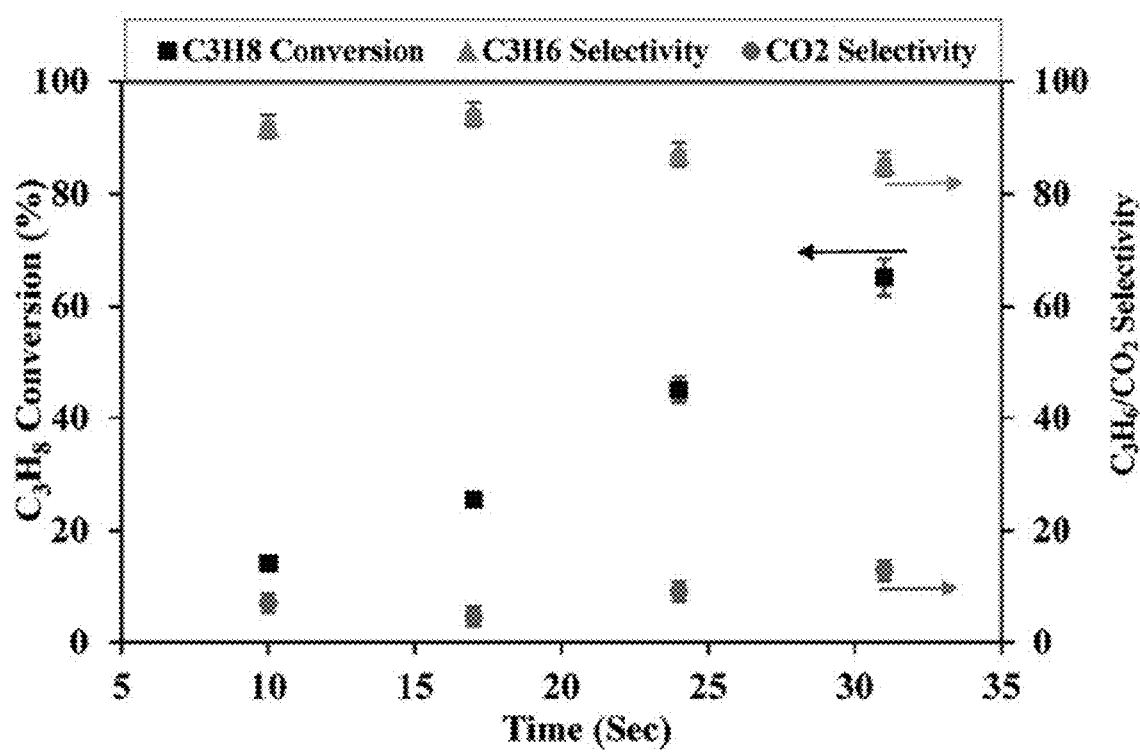
FIG. 9 is a graph of propane ($C_3H_8$) conversion and propylene ($C_3H_6$) and $CO_2$ selectivity and their error limits for the prepared catalysts in repeated oxidative dehydrogenation of propane reaction runs at a temperature of 640° C., catalyst loading of 0.5 g, and a propane injection amount of 1.2 mL.

In the catalytic runs, the reaction temperature was varied between 550 and 640° C., while the reaction time was attuned from 10 to 31 seconds. The product analysis of the preliminary runs contains unreacted propane, propylene and carbon dioxide. Under the studied reaction conditions, no hydrogen was detected, indicating the absence of cracking and/or dehydrogenation. FIG. 9 shows the propane ($C_3H_8$) conversion and propylene ($C_3H_6$) and $CO_2$ selectivity and their error limits in repeated runs. The propane conversion and product selectivity in the experimental repeats are found to be within 2.5% error limits (FIG. 9). Mass balances were established for each of the three repeat of each individual run and the mass balance closed consistently in excess of 95%. From the product analysis, one can consider the following three possible reaction steps during the fluidized ODH or propane in the absence of gas phase oxygen. Formula (VIII) gives the balanced equation of the ODH of propane to propylene reaction. Formula (XX) gives the equation of the complete oxidation of propane reaction. Formula (XXI) gives the equation of the complete oxidation of propylene reaction.

$$2C_3H_8 + V_2O_5 \rightarrow 2C_3H_6 + 2H_2O + V_2O_3 \tag{VIII}$$

$$C_3H_8 + 5V_2O_5 \rightarrow 3CO_2 + 4H_2O + 5V_2O_3 \tag{XX}$$

$$C_3H_6 + \frac{9}{2}V_2O_5 \rightarrow 3CO_2 + 3H_2O + \frac{9}{2}V_2O_3 \tag{XXI}$$

Therefore, it is important to identify reaction conditions in order to achieve the high propylene yields and suppress the complete combustion reactions which produce $CO_2$. With the above factors in mind, experiments were conducted under different conditions to demonstrate the effects of certain parameters on the propane conversion and product selectivity including, but not limited to, (i) the consecutive propane injection without catalyst regeneration, (ii) reaction temperatures, and (iii) contact times.

Figure 10:
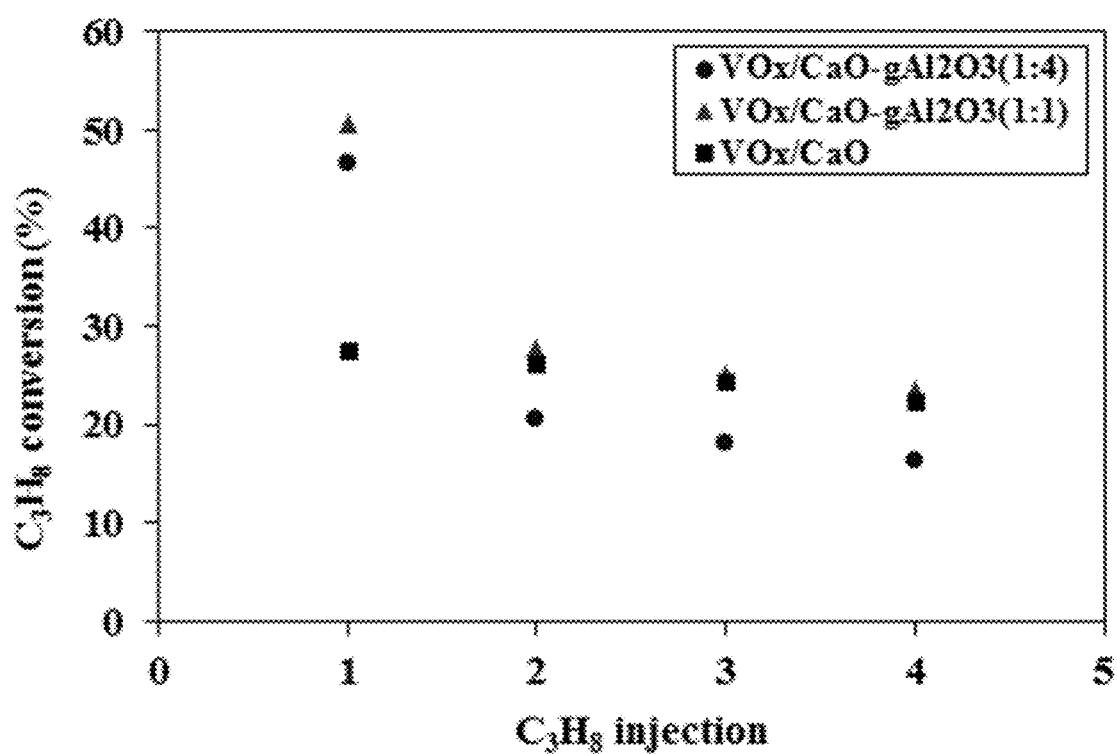
FIG. 10 is a graph of propane conversion for the prepared catalysts in successive propane injections without catalyst regeneration in oxidative dehydrogenation of propane reaction runs at a temperature of 640° C., catalyst loading of 0.5 g, a propane injection amount of 1.2 mL, and a contact reaction time of 17 seconds.
Figure 11:
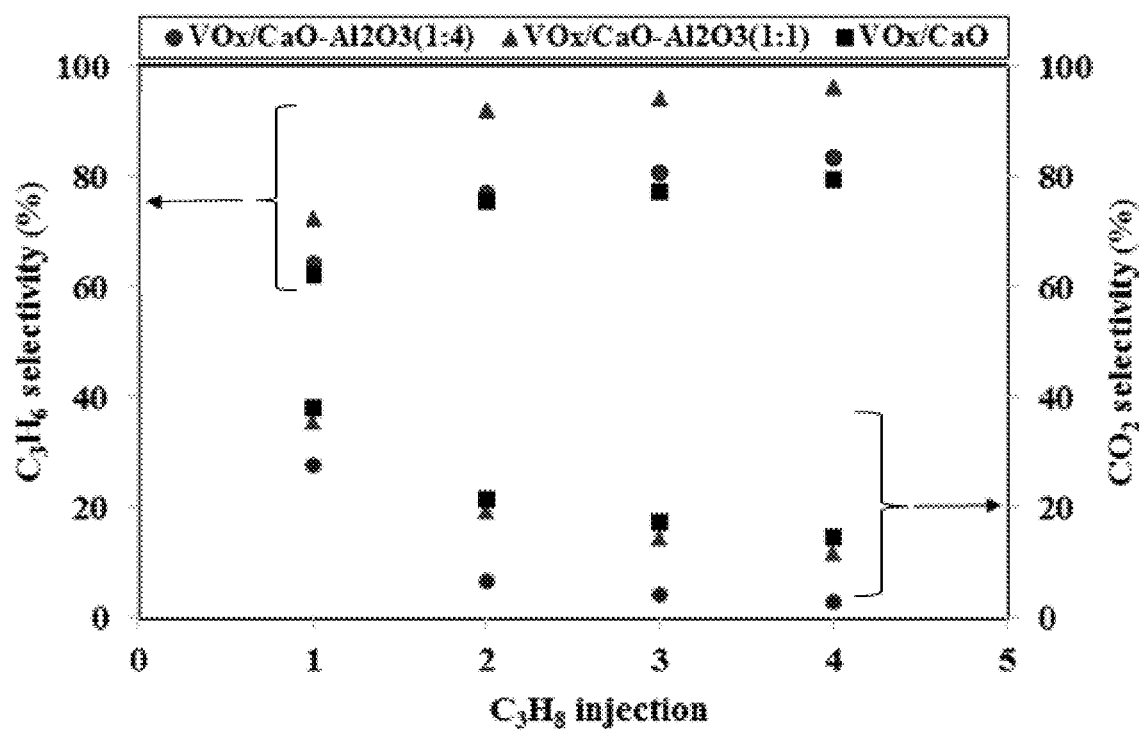
FIG. 11 is a graph of propylene and $CO_2$ selectivity for the prepared catalysts in successive propane injections without catalyst regeneration in oxidative dehydrogenation of propane reaction runs at a temperature of 640° C., catalyst loading of 0.5 g, a propane injection amount of 1.2 mL, and a contact reaction time of 17 seconds.

The successive oxidative dehydrogenation of propane experiments without catalyst regeneration were conducted to demonstrate the effects of the degree of catalyst reduction on the propane conversion and product distribution. To ensure the same reaction conditions, the reactor was loaded with 0.5 g of catalyst and the temperature was maintained at 640° C. Furthermore, in each run the same 1.2 mL of propane was injected and the reactions were allowed to proceed for a consistent 17 seconds. FIG. 10 plots the propane conversion over the successive injection of propane runs. FIG. 11 plots the propylene and carbon oxide product selectivity over the successive injection of propane runs. FIG. 10 demonstrates that all three $VO_x/CaO$—$\gamma$-$Al_2O_3$ catalysts give their highest propane conversion in the first injection, which gradually decreases in the following successive propane injections. The availability of the oxygen at the catalyst surface mainly contributed to the high propane conversion in the first injection. The appreciable levels of catalyst activity after all four successive injections can be attributed to the lattice oxygen availability in the catalyst matrix. In contrast, the diminishing trend of the propane conversion is due to the progressive consumption of the lattice oxygen in the catalysts. Among the three catalysts, $VO_x/CaO$-$\gamma$-$Al_2O_3$ (1:1) displays the highest propane conversion (51%) and propylene selectivity. This is consistent with its moderate acidity, moderate active site metal-support interactions and balanced oxygen carrying capacity in comparison to the other two catalysts as observed in the TPR analysis.

FIG. 11 demonstrates that the selectivity of both the desired propylene and undesired carbon dioxide vary significantly during the successive propane injection runs. In contrast to propane conversion, the first injection gives the lowest propylene selectivity and highest carbon dioxide selectivity. This indicates that the surface oxygen favors the complete oxidation of propane/propylene and the production of carbon dioxide. The propylene selectivity significantly increased in the second injection and subsequently the incremental increases became minimal in the remaining runs although there is an increasing trend still evident. This variation in selectivity indicates that certain amounts of lattice oxygen are required to maximize selectivity to propylene and minimize selectivity to carbon dioxide.

This observation is in line with the fact that selectivity to propylene in the oxidative dehydrogenation of propane over $VO_x$ based catalysts is affected positively by the energy that binds the lattice oxygen with the catalyst [S. A. Al-Ghamdi, M. M. Hossain, H. I. de Lasa, Kinetic modeling of ethane oxidative dehydrogenation over $VOx/Al_2O_3$ catalyst in a fluidized-bed riser simulator, Ind. Eng. Chem. Res. 52 (2013) 5235-5244.—incorporated herein by reference in its entirety]. At higher oxidation states of the catalyst the binding energy of the lattice oxygen is low (low active site metal-support interaction), which eventually leads to combustion of propane/propylene to carbon oxides. Furthermore, the surface oxygen atoms on the fresh or regenerated catalyst are loosely bonded with the catalysts, which easily react with propane/propylene to produce carbon dioxide. In this case, a selective catalyst surface would be obtained only after the adsorbed oxygen of the bulk $V_2O_5$ like surface species has been consumed via the first propane injection. It was after the consumption of adsorbed oxygen through the first propane injection that higher selectivity at the catalyst surface could be obtained.

When compared, $VO_x/CaO$-$\gamma$-$Al_2O_3$ (1:1) shows significantly higher propylene selectivity and much lower carbon dioxide selectivity that that of the $VO_x/CaO$ catalyst. This catalyst shows up to 96% propylene selectivity while the higher CaO containing catalysts produce up to 83% propylene selectivity. This can be attributed to the moderate level of acidity of $VO_x/CaO$-$\gamma$-$Al_2O_3$ (1:1) as demonstrated by the $NH_3$-TPD results. This observation is also consistent with the XRD and TPR results. The proper balance of $CaO/Al_2O_3$ influences the $VO_x$ dispersion forming more isolated non-crystalline $VO_x$ species, which favors the propylene formation and suppresses the complete oxidation to $CO_2$. Furthermore, the increased V-support interaction with the CaO promoted sample, as revealed by the TPD kinetics analysis, may also explain the controlled ODH reaction between propane and the lattice oxygen of the catalyst, resulting in enhanced propylene selectivity. Works have been published on ODH selectivity as a function of the oxidation state of vanadium based catalysts [V. Balcaen, I. Sack, M. Olea, G. B. Marin, Transient kinetic modeling of the oxidative dehydrogenation of propane over a vanadia-based catalyst in the absence of $O_2$, Appl. Catal. A: Gen. 371 (2009) 31-42; and O. S. Owen, M. C. Kung, H. Kung, The effect of oxide structure and cation reduction potential of vanadates on the selective oxidative dehydrogenation of butane and propane, Catal. Lett. 12 (1992) 45-50; and Creaser D, Andersson B, Hudgins R R, Silverston P L, Transient kinetic analysis of the oxidative dehydrogenation of propane, J. Catal. 182 (1999) 264-269.—each incorporated herein by reference in its entirety]. These published works were focused on ODH reactions that utilize successive injections of alkanes in the absence of gas phase oxygen and indicate that high selectivity for alkenes in ODH reactions can be obtained at certain lattice oxygen of the vanadium based catalyst. Lopex-Nitro, et al. found that the selectivity to propylene and butylene with respective usage of propane and butane as the feed could be strongly influenced by the reducibility of the vanadium based catalyst. Balcaen, et al. also observed the same tend of ODH or propane over a vanadium based catalyst [V. Balcaen, I. Sack, M. Olea, G. B. Marin, Transient kinetic modeling of the oxidative dehydrogenation of propane over a vanadia-based catalyst in the absence of $O_2$, Appl. Catal. A Gen. 371 (2009) 31-42.—incorporated herein by reference in its entirety]. Studies by Al-Ghamdi, et al. on ethane ODH over $\gamma$-Alumina supported vanadium catalyst in the absence of gas phase oxygen is important for the selective conversion of alkane to alkene with the binding energy of lattice oxygen as the main driver of the reaction.

Figure 12:
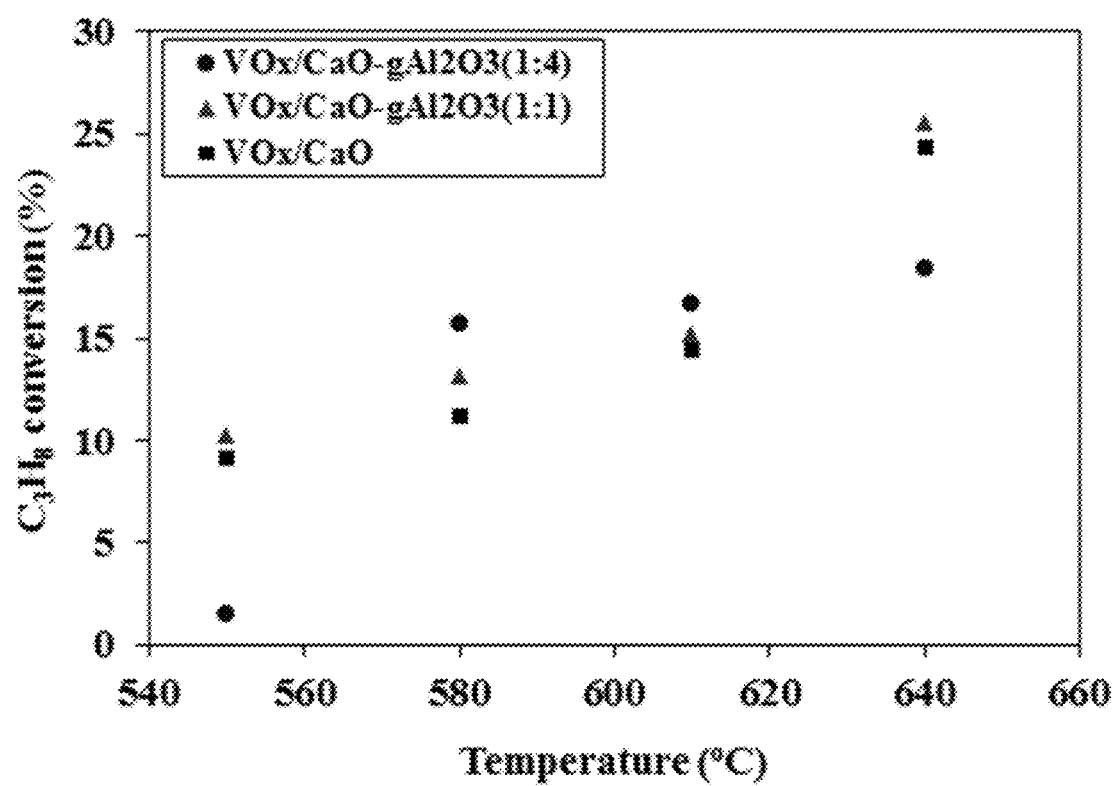
FIG. 12 is a graph of propane conversion for the prepared catalysts at different temperatures in oxidative dehydrogenation of propane reaction runs at a catalyst loading of 0.5 g, a propane injection amount of 1.2 mL, and a contact reaction time of 17 seconds.
Figure 13:
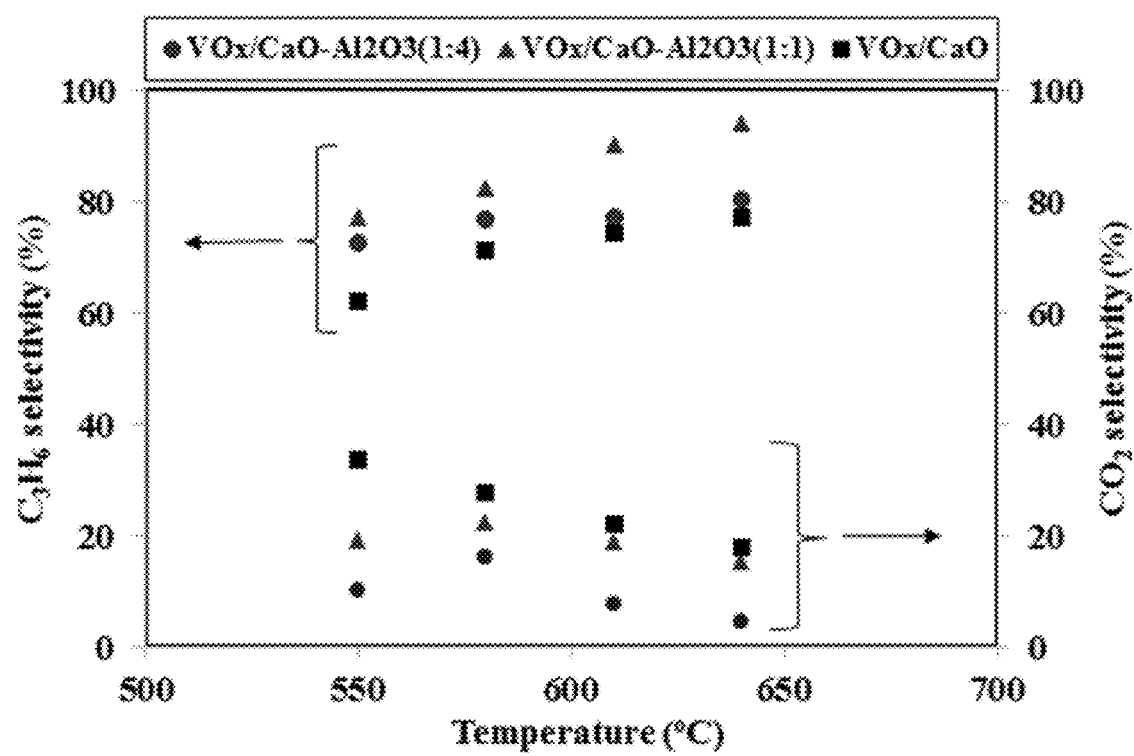
FIG. 13 is a graph of propylene and $CO_2$ selectivity for the prepared catalysts at different temperatures in oxidative dehydrogenation of propane reaction runs at a catalyst loading of 0.5 g, a propane injection amount of 1.2 mL, and a contact reaction time of 17 seconds.

FIG. 12 presents propane conversion at different reaction temperatures and a constant 17 second contact reaction time. FIG. 13 presents product selectivity for the desired propylene and undesired carbon dioxide at different reaction temperatures and a constant 17 second contact reaction time. These runs are conducted using oxidized catalysts. After each run the catalyst was re-oxidized by circulating air through the catalyst bed. It can be seen that the $VO_x/CaO$-$\gamma$-$Al_2O_3$ (1:4) sample shows very low conversion at 550° C., which is consistent with its higher initial reduction temperature as observed in the TPR analysis (FIG. 6). The $VO_x/CaO$—$\gamma$-$Al_2O_3$ (1:4) sample is mainly reduced between 520° C. and 580° C. Therefore, there is only a small fraction of lattice oxygen available for reaction at 550° C. In contrast, both the $VO_x/CaO$-$\gamma$-$Al_2O_3$ (1:1) and $VO_x/CaO$ catalyst samples show some reduction at low temperatures, which may contribute to the higher propane conversions at 550° C. when using these two samples. Propane conversion increased with the increasing reaction temperature as the lattice oxygen of the catalyst activates at higher temperature (FIG. 6, TPR analysis). Interestingly, with increasing the reaction temperature, all the catalyst samples showed increased propylene selectivity and decreased carbon dioxide selectivity (FIG. 13). The variation in the degree of reduction of the catalyst with reaction temperatures was likely responsible for the rise in the selectivity of propylene. At higher temperatures, the degree of catalyst reduction increases (FIG. 6, TPR analysis) as a result of the lower binding energy of lattice oxygen. At such higher degrees of reduction of the catalysts, the selective pathway toward ODH is preferred over that for combustion as observed in the successive propane injection experimental runs. The good selectivity to propylene can also be attributed to the non-formation of larger molecules due to the interaction of the mixed support and the active site of each catalyst, as detected by XRD. Among the three studied catalysts, $VO_x/CaO$-γ-$Al_2O_3$ (1:1) shows the highest propylene selectivity. The carbon dioxide selectivity with this catalyst is also lower than that of the $VO_x/CaO$ catalyst while slightly higher than the $VO_x/CaO$-γ-$Al_2O_3$ (1:4) catalyst. The superior propylene selectivity of the $VO_x/CaO$-γ-$Al_2O_3$ (1:1) catalyst can be attributed to the moderate level of acidity of $VO_x/CaO$-γ-$Al_2O_3$ (1:1) as demonstrated by the $NH_3$-TPD results.

Figure 14:
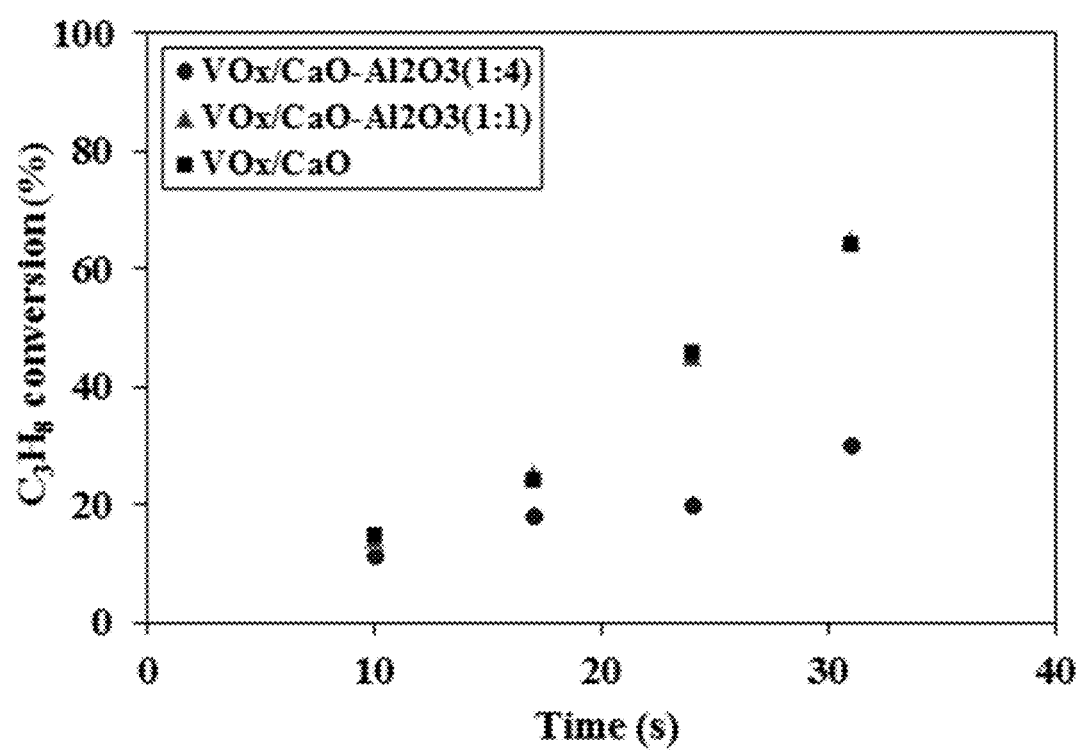
FIG. 14 is a graph of propane conversion for the prepared catalysts at different contact reaction times in oxidative dehydrogenation of propane reaction runs at a temperature of 640° C., catalyst loading of 0.5 g, and a propane injection amount of 1.2 mL.
Figure 15:
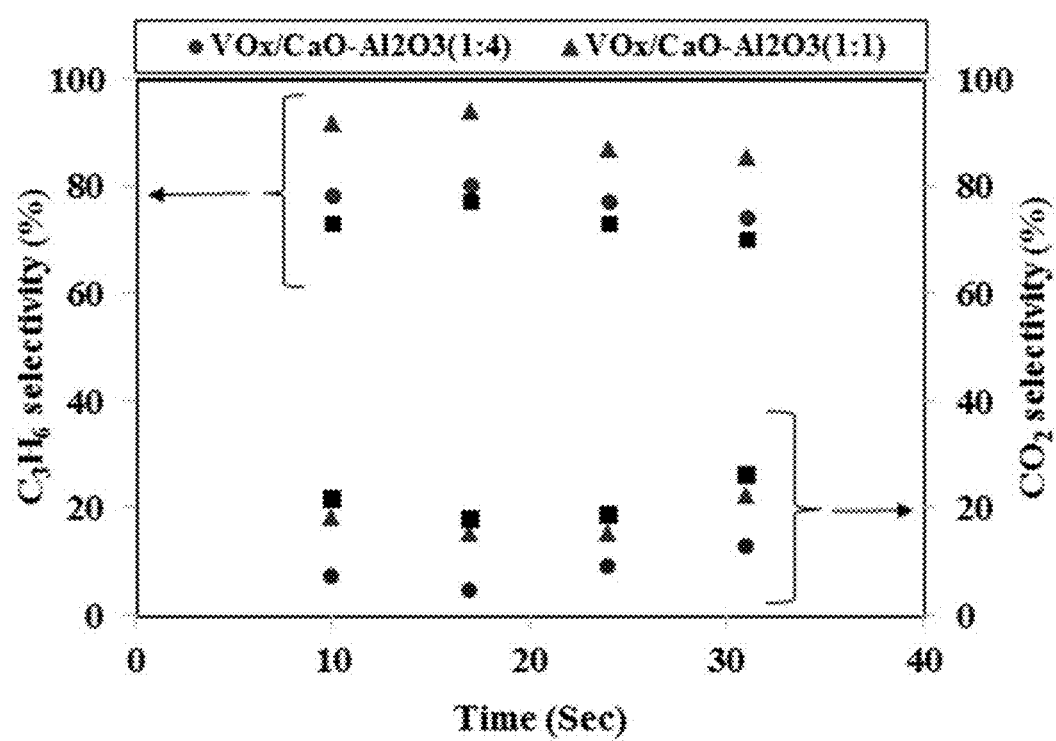
FIG. 15 is a graph of propylene and $CO_2$ selectivity for the prepared catalysts at different contact reaction times in oxidative dehydrogenation of propane reaction runs at a temperature of 640° C., catalyst loading of 0.5 g, a propane injection amount of 1.2 mL.

Propane ODH experiments were carried out at 10, 17, 24 and 31 seconds in order to study the effect of reaction time on propane conversion, propylene selectivity and carbon dioxide selectivity at a temperature of 640° C. FIG. 14 presents propane conversion at different reaction times and a constant 640° C. reaction temperature. FIG. 15 presents product selectivity for the desired propylene and undesired carbon dioxide at different reaction times and a constant 640° C. reaction temperature. It is evident that propane conversion for all catalyst samples increases with the reaction time (FIG. 14). The propylene selectivity slightly increases from 10 to 17 seconds and after that it decreases with reaction contact time above 17 seconds. Conversely, the carbon dioxide selectivity slightly decreases from 10 to 17 seconds and increases from 17 to 31 seconds (FIG. 15). The decrease of propylene selectivity and increase of carbon dioxide selectivity at higher contact time are mainly due to the consecutive oxidation of propylene and/or complete oxidation of propane to carbon dioxide.

Therefore, the higher contact times favor high propane conversions while some contact time favor high propylene selectivity and low carbon oxide selectivity. The good selectivity to propylene obtained from the three catalyst samples can be attributed to the high proportion of mono-vanadate $VO_x$ species which was detected from the laser Raman spectroscopy result. Again, the $VO_x/CaO$-γ-$Al_2O_3$ (1:1) catalyst shows the highest propane conversion and propylene selectivity and lowest carbon oxide selectivity. This can be attributed to the moderate level of acidity of the $VO_x/CaO$-γ-$Al_2O_3$ (1:1) catalyst as depicted in the $NH_3$-TPD results.

Thus, one can conclude that the performance of the $VO_x/CaO$-γ-$Al_2O_3$ (1:4), $VO_x/CaO$-γ-$Al_2O_3$ (1:1), and $VO_x/CaO$ catalyst samples is strongly influenced by both reaction contact times and temperatures and also catalyst regeneration. It can be inferred that successive feed injections are the best for the ODH reaction; hence it is only on completion of the successive reaction cycles that catalyst could be regenerated. This can be applied industrially using a fluidized bed reactor that has reactor-generator compartments and has the ability to transfer only a small percentage of the catalyst to the regenerator.

Figure 16:
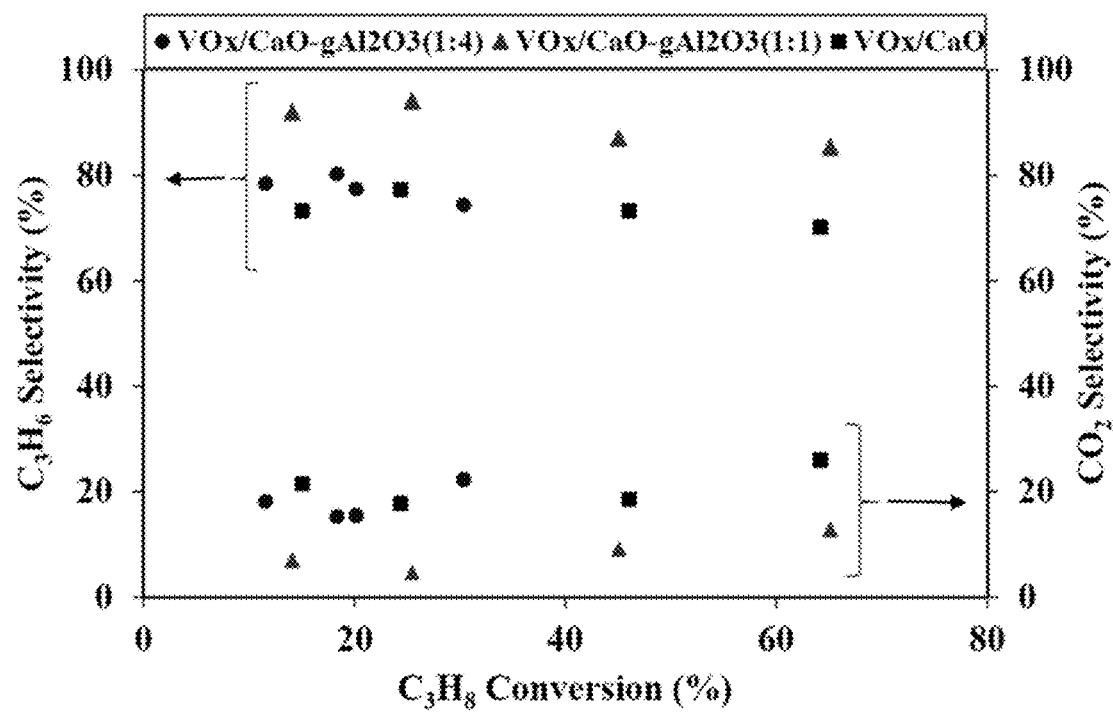
FIG. 16 is a graph of propylene and $CO_2$ selectivity for the prepared catalysts as a function of propane conversion for the prepared catalysts at constant temperature in oxidative dehydrogenation of propane reaction runs at a temperature of 640° C., catalyst loading of 0.5 g, and a propane injection amount of 1.2 mL.

FIG. 16 presents propylene and carbon dioxide selectivities as a function of propane conversion at constant temperature. It is evident that with increasing propane conversion, propylene selectivity decreases which is compensated for by an increasing $CO_2$ selectivity. All the three catalyst samples show similar trends. This indicates that propylene is the primary reaction product of propane while $CO_2$ comes from deep oxidation of propane as well as consecutive oxidations of propane and propylene.

Table 4 compares the performance of the catalyst of the present disclosure $VO_x/CaO$-γ-$Al_2O_3$ (1:1) with the performance of the ODH catalysts reported in the past literature [T. V. M. Rao, G. Deo, Kinetic Parameter Analysis for Propane ODH: $V_2O_5/Al_2O_3$ and $MoO_3/Al_2O_3$ Catalysts, AIChE J. 53 (2007) 2432-2442.—incorporated herein by reference in its entirety]. There is an appreciable comparison of the propylene selectivity of the $VO_x/CaO$-γ-$Al_2O_3$ (1:1) catalyst with the other catalysts as shown. This indicates that the ODH of propane with lattice oxygen (gas phase oxygen free conditions) is promising to enhance the propylene selectivity even at higher propane conversion.

TABLE 4

Comparison of the performance of the prepared $VO_x/CaO$-γ-$Al_2O_3$ (1:1) catalyst with that of other ODH catalysts previously reported in the literature

| Catalyst | Reactivity temperature (° C.) | Propane conversion % (at highest selectivity) | Highest propylene selectivity % | Reference |
| --- | --- | --- | --- | --- |
| 17.5% MoO/γ-$Al_2O_3$ | 380 | 1.3 | 77 | Rao, et al. |
| 17.5% MoO/γ-$Al_2O_3$ | 380 | 1.7 | 83 | Rao, et al. |
| 5% $VO_x$/γ-$Al_2O_3$ | 550 | 11.7 | 86 | Al-Ghamdi, et al. |
| $VO_x/CaO$-γ-$Al_2O_3$ (1:4) | 525-600 | 65.1 | 85.2 | Current Disclosure |

In conclusion, FTIR, Raman and XRD detected $V_2O_5$, CaO, and γ-$Al_2O_3$ species in the prepared and synthesized catalysts, the XRD showed a very small amount of crystalline $VO_x$ phases, the remaining $VO_x$ appeared as an amorphous phase which is favorable for selective oxidations. The isolated VOx phases, as observed by FTIR spectroscopy and XRD, are favorable towards higher propylene selectivity. SEM images and elemental mapping showed good vanadium oxide dispersion of the catalytic material on the mixed CaO-γ-$Al_2O_3$ support. Repeated TPR/TPO experiments showed the consistent reduction and reoxidation behavior of the prepared catalysts as well as the increase in oxygen carrying capacity with increasing CaO content. Furthermore, $NH_3$-TPD analysis revealed that the acidity of the catalysts were progressively decreased with increasing CaO content and the activation energy of ammonia desorption decreased with increasing amounts of CaO reflecting the increased active site metal-support interactions which may control the reaction of the lattice oxygen and favor propylene as a selective product in ODH reactions of propane. Under gas phase oxygen free conditions the oxidative dehydrogenation of propane in the presence of the catalysts favored the selective formation of propylene product and minimized the complete oxidations to $CO_x$ products. In addition, a higher degree of catalyst reductions gave more selective products. The prepared catalyst with intermediate acidity and moderate active site metal-support interactions ($VO_x/CaO$-$\gamma$-$Al_2O_3$ (1:1)) displayed the highest propylene selectivity (85%) at higher propane conversion (65%).

Thus, the foregoing discussion discloses and describes merely exemplary embodiments of the present invention. As will be understood by those skilled in the art, the present invention may be embodied in other specific forms without departing from the spirit or essential characteristics thereof. Accordingly, the disclosure of the present invention is intended to be illustrative, but not limiting of the scope of the invention, as well as other claims. The disclosure, including any readily discernible variants of the teachings herein, defines, in part, the scope of the foregoing claim terminology such that no inventive subject matter is dedicated to the public.

The invention claimed is:

1. A dehydrogenation catalyst, comprising:
   a support material comprising alumina modified by calcium oxide, wherein a weight ratio of calcium oxide to alumina is from 1:0.2 to 1:8; and
   a catalytic material comprising one or more vanadium oxides disposed on the support material;
   wherein the dehydrogenation catalyst comprises 5-20% of the one or more vanadium oxides by weight relative to the total weight of the dehydrogenation catalyst.

2. The dehydrogenation catalyst of claim 1, wherein the weight ratio of calcium oxide to alumina is 1:1.

3. The dehydrogenation catalyst of claim 1, wherein the one or more vanadium oxides form an amorphous phase on the surface of the support material.

4. The dehydrogenation catalyst of claim 1, wherein the one or more vanadium oxides are at least one selected from the group consisting of $V_2O_5$, $VO_2$, and $V_2O_3$.

5. The dehydrogenation catalyst of claim 4, which comprises at least 50% of $V_2O_5$ by weight relative to the total weight of the one or more vanadium oxides.

6. The dehydrogenation catalyst of claim 1, which has an average particle size in the range of 20-160 μm.

7. The dehydrogenation catalyst of claim 1, which has an apparent particle density in the range of 1-10 g/cm³.

8. The dehydrogenation catalyst of claim 1, which has a BET surface area in the range of 5-50 m²/g.

9. The dehydrogenation catalyst of claim 1, which is fluidizable and has Class B powder properties in accordance with Geldart particle classification.

10. A method for producing the dehydrogenation catalyst of claim 1, comprising:
    mixing alumina with calcium oxide and a vanadyl coordination complex or salt in a solvent to form loaded catalyst precursors;
    reducing the loaded catalyst precursors with $H_2$ gas to form reduced catalyst precursors; and
    oxidizing the reduced catalyst precursors with oxygen to form the dehydrogenation catalyst.

11. A method for dehydrogenating an alkane to a corresponding olefin comprising flowing the alkane through a reactor comprising a catalyst chamber loaded with the dehydrogenation catalyst of claim 1 at a temperature in the range of 400-800° C. to form the corresponding olefin and a reduced catalyst.

12. The method of claim 11, wherein the reactor is a fluidized bed reactor and the dehydrogenating is performed in a gas phase oxygen free environment.

13. The method of claim 11, wherein the alkane is propane and the corresponding olefin is propylene.

14. The method of claim 11, further comprising:
    oxidizing at least a portion of the reduced catalyst in a gas phase oxygen environment separated from the catalyst chamber to regenerate the dehydrogenation catalyst; and
    repeating the flowing and the oxidizing at least once with a less than 10% decrease in percent conversion of the alkane, a less than 10% decrease in selectivity for the olefin relative to a total percentage of products formed, or both.

15. The method of claim 11, wherein the dehydrogenation catalyst is present at an amount in the range of 0.05-1.0 g of catalyst per mL of alkane.

16. The method of claim 11, wherein the alkane is propane and the method has a propane conversion of 10-80% at a reaction time of 5-60 seconds and a temperature of 500-700° C.

17. The method of claim 11, wherein the alkane is propane and the method has a propylene selectivity of at least 60% relative to a total percentage of products formed at a reaction time of 5-60 seconds and a temperature of 500-700° C.

18. The method of claim 11, wherein the alkane is propane and the method has a carbon dioxide selectivity of no more than 40% relative to a total percentage of products formed at a reaction time of 5-60 seconds and a temperature of 500-700° C.

19. The method of claim 11, wherein the alkane is propane, the dehydrogenation catalyst has a weight ratio of calcium oxide to alumina of 1:1, and the method has a propane conversion of at least 60% and a propylene selectivity of at least 80% relative to a total percentage of products formed.

* * * * *